US007941275B2

(12) United States Patent
Gholap et al.

(10) Patent No.: US 7,941,275 B2
(45) Date of Patent: May 10, 2011

(54) METHOD AND SYSTEM FOR AUTOMATED DETECTION OF IMMUNOHISTOCHEMICAL (IHC) PATTERNS

(75) Inventors: Abhijeet S. Gholap, San Jose, CA (US); Gauri A. Gholap, San Jose, CA (US); Chiruvolu V. K. Rao, Pune (IN); Sanford H. Barsky, Columbus, OH (US); Madhura Vipra, Pune (IN); Gurunath Kamble, Pune (IN); Suhas Manmantrao Patil, Pune (IN); Prithviraj Jadhav, Pune (IN)

(73) Assignee: Ventana Medical Systems, Inc., Tucson, AZ (US)

( * ) Notice: Subject to any disclaimer, the term of this patent is extended or adjusted under 35 U.S.C. 154(b) by 533 days.

(21) Appl. No.: 11/091,614

(22) Filed: Mar. 27, 2005

(65) Prior Publication Data
US 2006/0014238 A1  Jan. 19, 2006

Related U.S. Application Data

(63) Continuation-in-part of application No. 10/938,314, filed on Sep. 10, 2004, application No. 11/091,614, which is a continuation-in-part of application No. 10/966,071, filed on Oct. 15, 2004, now abandoned.

(60) Provisional application No. 60/556,844, filed on Mar. 27, 2004, provisional application No. 60/501,412, filed on Sep. 10, 2003, provisional application No. 60/515,582, filed on Oct. 30, 2003, provisional application No. 60/530,174, filed on Dec. 15, 2003.

(51) Int. Cl.
*G01N 33/48* (2006.01)
*G06K 9/00* (2006.01)

(52) U.S. Cl. ............................ 702/19; 382/128; 702/20

(58) Field of Classification Search ........................ None
See application file for complete search history.

(56) References Cited

U.S. PATENT DOCUMENTS

| 4,724,543 | A  | 2/1988  | Klevecz        |
|-----------|----|---------|----------------|
| 5,018,209 | A  | 5/1991  | Bacus          |
| 5,526,258 | A  | 6/1996  | Bacus          |
| 5,546,323 | A  | 8/1996  | Bacus et al.   |
| 6,009,342 | A  | 12/1999 | Brasch et al.  |
| 6,151,405 | A  | 11/2000 | Douglass       |
| 6,215,892 | B1 | 4/2001  | Douglass       |
| 6,330,349 | B1 | 12/2001 | Hays           |
| 6,365,362 | B1 | 4/2002  | Terstappen     |
| 6,404,916 | B1 | 6/2002  | Torre-Bueno    |
| 6,418,236 | B1 | 7/2002  | Ellis          |
| 6,445,817 | B1 | 9/2002  | Torre-Bueno    |
| 6,479,493 | B1 | 11/2002 | Whitehead      |
| 6,518,554 | B1 | 2/2003  | Zhang          |
| 6,546,123 | B1 | 4/2003  | McLaren        |
| 6,553,135 | B1 | 4/2003  | Douglass       |
| 6,605,342 | B1 | 8/2003  | Burghaus et al.|
| 6,631,203 | B2 | 10/2003 | Ellis          |
| 6,645,731 | B2 | 11/2003 | Terstappen     |
| 6,671,393 | B2 | 12/2003 | Hays           |
| 6,674,881 | B2 | 1/2004  | Bacus          |
| 6,674,884 | B2 | 1/2004  | Bacus          |
| 6,674,896 | B1 | 1/2004  | Torre-Bueno    |
| 6,697,509 | B2 | 2/2004  | Torre-Bueno    |
| 6,711,283 | B1 | 3/2004  | Soenksen       |
| 6,718,053 | B1 | 4/2004  | Ellis          |
| 6,768,511 | B1 | 7/2004  | Nakai          |
| 6,775,402 | B2 | 8/2004  | Bacus          |
| 6,800,249 | B2 | 10/2004 | Torre-Bueno    |
| 6,900,426 | B2 | 5/2005  | Zhang          |
| 6,911,315 | B2 | 6/2005  | Rimm           |
| 6,914,613 | B2 | 7/2005  | Marchand       |
| 6,917,696 | B2 | 7/2005  | Soenksen       |
| 6,920,239 | B2 | 7/2005  | Douglass       |
| 2002/0009759 | A1 | 1/2002 | Terstappen     |
| 2002/0061542 | A1 | 5/2002 | Rimm           |
| 2002/0168657 | A1 | 11/2002| Chen           |
| 2002/0172987 | A1 | 11/2002| Terstappen     |
| 2003/0045451 | A1 | 3/2003 | Bacus          |
| 2003/0049701 | A1 | 3/2003 | Muraca         |
| 2003/0068626 | A1 | 4/2003 | Wang           |
| 2003/0073096 | A1 | 4/2003 | Bao            |
| 2003/0092047 | A1 | 5/2003 | LaMorte et al. |
| 2003/0096261 | A1 | 5/2003 | Fruehauf       |
| 2003/0129676 | A1 | 7/2003 | Terstappen     |

(Continued)

FOREIGN PATENT DOCUMENTS
EP           0283255         9/1988
(Continued)

OTHER PUBLICATIONS

Albert, et al. New method of nuclear grading of tissue sections by means of digital image analysis with prognostic significance for node-negative breast cancer patients. Cytometry. 1996; 24(2):140-50.
Comaniciu, et al. image-guided decision support system for pathology. Machine Vision and Applications. Springer, Verlag, DE. 1999; 11(4): 213-224.
Drezet, et al. Automatic mitotic index estimation for the prognostication of breast cancer from histology images. IEE Colloquium Intelligent Methods in Healthcare and Medical Applications. Oct. 20, 1998. pp. 14-1.
Gao, et al. Computer-aided prostate cancer diagnosis using image enhancement and JPEG 2000. Proceedings—SPIE the International Society for Optical Eng. International Society for Optical Engineering; Applications of Digital Image Processing XXVI. 2003; 5203;323-334.
Hatanaka, et al. Quantitative immunohistochemical evaluation of HER2/neu expression with HercepTestTM in breast carcinoma by image analysis. Pathol Int. 2001; 51(1):33-6.
Kate, et al. Method for counting mitoses by image processing in Feulgen stained breast cancer sections. Cytometry. 1993;14(3):241-50.

(Continued)

*Primary Examiner* — Shubo (Joe) Zhou
(74) *Attorney, Agent, or Firm* — Wilson Sonsini Goodrich & Rosati

(57) ABSTRACT

A method and system for automated detection of immunohistochemical (IHC) patterns. The method and system is able to automatically differentiate an epithelial cell part from a non-epithelial cell part of a digital image of a tissue sample to which an IHC compound has been applied. The method and system help to automatically correct errors made in a manual interpretation of a pathological or other manual analysis of tissue samples for diseases such as a human cancer.

23 Claims, 17 Drawing Sheets

U.S. PATENT DOCUMENTS

| | | |
|---|---|---|
| 2003/0165263 A1 | 9/2003 | Hamer |
| 2003/0168577 A1 | 9/2003 | Zhang |
| 2003/0170703 A1 | 9/2003 | Piper |
| 2003/0215936 A1 | 11/2003 | Kallioniemi |
| 2003/0231791 A1 | 12/2003 | Torre-Bueno |
| 2004/0004614 A1 | 1/2004 | Bacus |
| 2004/0009098 A1 | 1/2004 | Torre-Bueno |
| 2004/0066960 A1 | 4/2004 | McLaren et al. |
| 2004/0071327 A1 | 4/2004 | Ellis |
| 2004/0081345 A1 | 4/2004 | Douglass |
| 2004/0085443 A1 | 5/2004 | Kallioniemi |
| 2004/0115692 A1 | 6/2004 | Linder |
| 2004/0136582 A1 | 7/2004 | Bacus |
| 2004/0141637 A1 | 7/2004 | Bacus |
| 2004/0167806 A1 | 8/2004 | Eichhorn |
| 2004/0169883 A1 | 9/2004 | Eichhorn |
| 2004/0170312 A1 | 9/2004 | Soenksen |
| 2004/0170325 A1 | 9/2004 | Eichhorn |
| 2004/0171036 A1 | 9/2004 | Wang |
| 2004/0171091 A1 | 9/2004 | Lesko |
| 2004/0176277 A1 | 9/2004 | Sowadski |
| 2004/0176372 A1 | 9/2004 | Suto |
| 2004/0180889 A1 | 9/2004 | Suto |
| 2004/0191854 A1 | 9/2004 | Lapen |
| 2004/0202357 A1 | 10/2004 | Perz |
| 2004/0210547 A1 | 10/2004 | Wentland |
| 2004/0214872 A1 | 10/2004 | Suto |
| 2004/0236773 A1 | 11/2004 | Bacus |
| 2004/0252875 A1 | 12/2004 | Crandall |
| 2004/0256538 A1 | 12/2004 | Olson |
| 2005/0003464 A1 | 1/2005 | Tibbe |
| 2005/0004024 A1 | 1/2005 | Tibbitts |
| 2005/0037406 A1 | 2/2005 | Torre-Bueno |
| 2005/0069900 A1 | 3/2005 | Lentrichia |
| 2005/0070020 A1 | 3/2005 | Klautky |
| 2005/0136493 A1 | 6/2005 | Rubin |
| 2005/0136509 A1 | 6/2005 | Gholap et al. |
| 2005/0136549 A1 | 6/2005 | Gholap et al. |
| 2005/0181463 A1 | 8/2005 | Rao |
| 2005/0266395 A1 | 12/2005 | Gholap et al. |

FOREIGN PATENT DOCUMENTS

| | | |
|---|---|---|
| JP | 2000/224595 | 8/2000 |
| WO | WO 03/105675 | 12/2003 |

OTHER PUBLICATIONS

Krtolica, et al. Quantification of epithelial cells in coculture with fibroblasts by fluorescence image analysis. Cytometry. 2002; 49(2):73-82.

Madachy, et al. Image analysis for automatic classification of miotic cervical cells. Proceedings of the Annual International Conference of the IEEE Enginerring in Medicine and Biology Society. Nov. 4, 1988. pp. 372-374.

Rodenacker, et al. A feature set for cytometry on digitized microscopic images. Anal Cell Pathol. 2003; 25(1):1-36.

Sunbland, et al. The use of image analysis and automation for measuring mitotic index in apical conifer meristems. Journal of Experimental Botany. 1998; 49:1749-1756.

Van Der Laak, et al. Development and validation of a computerized cytomorphometric method to assess the maturation of vaginal epithelial cells. Cytometry. 1999; 35(3):196-202.

Weyn, et al. Automated breast tumor diagnosis and grading based on wavelet chromatin texture description. Cytometry. 1998; 33(1):32-40.

Gallart Biotech. Monoclonal Antibody Index. vol. 1: cancer. Available at: http://www.gallartinternet.com/mai. Accessed on Aug. 4, 2008.

Guassian Kernel

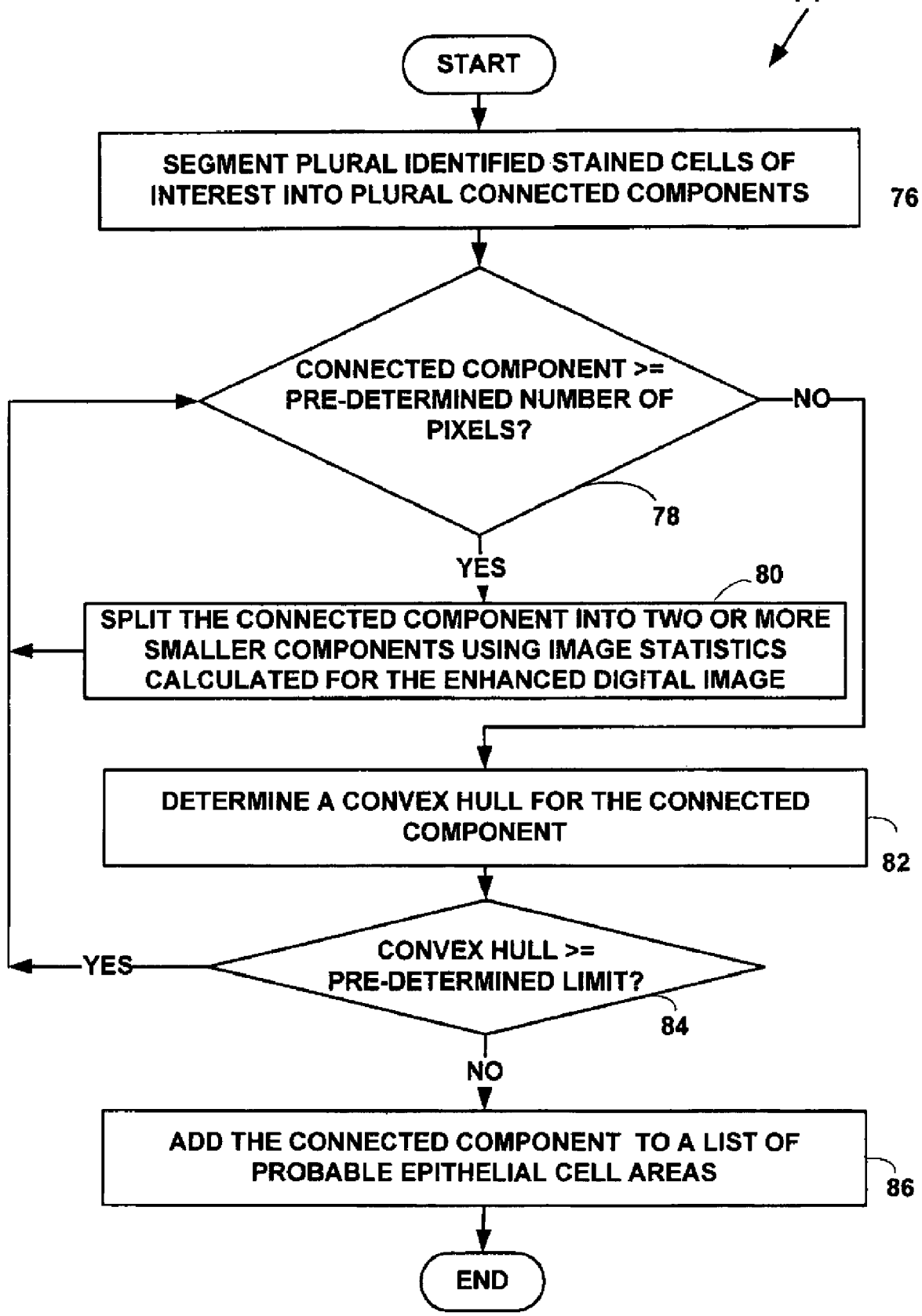

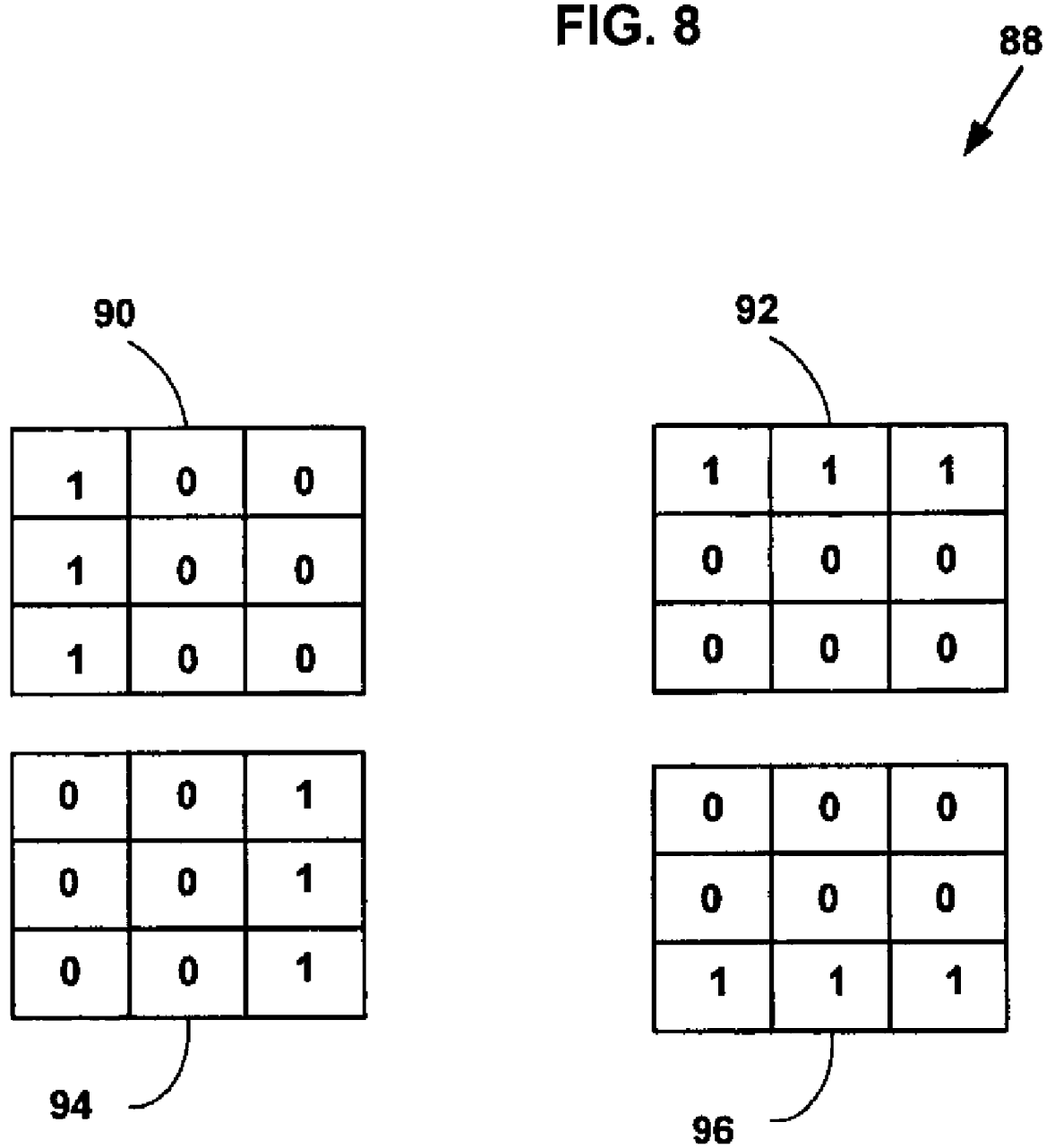

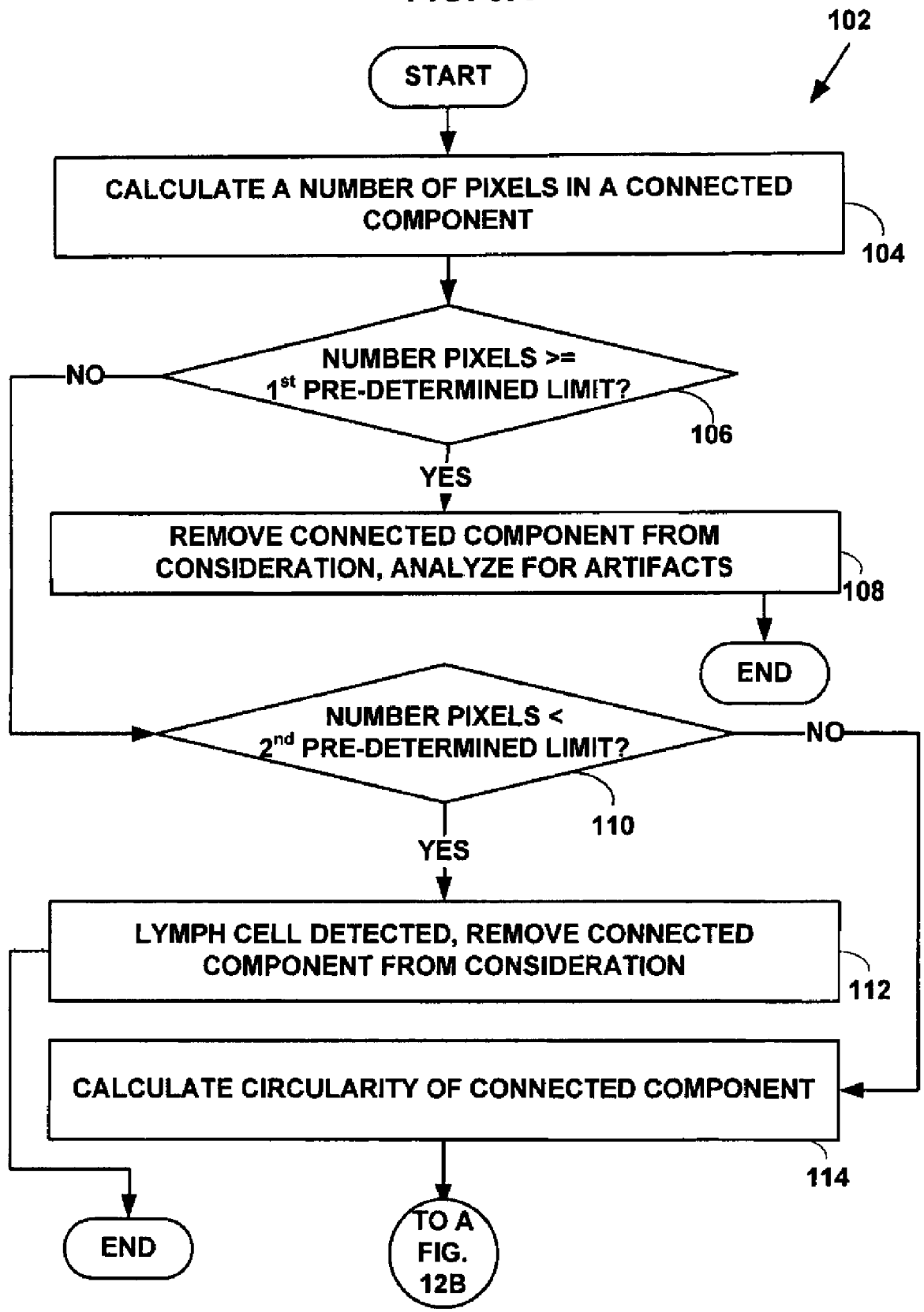

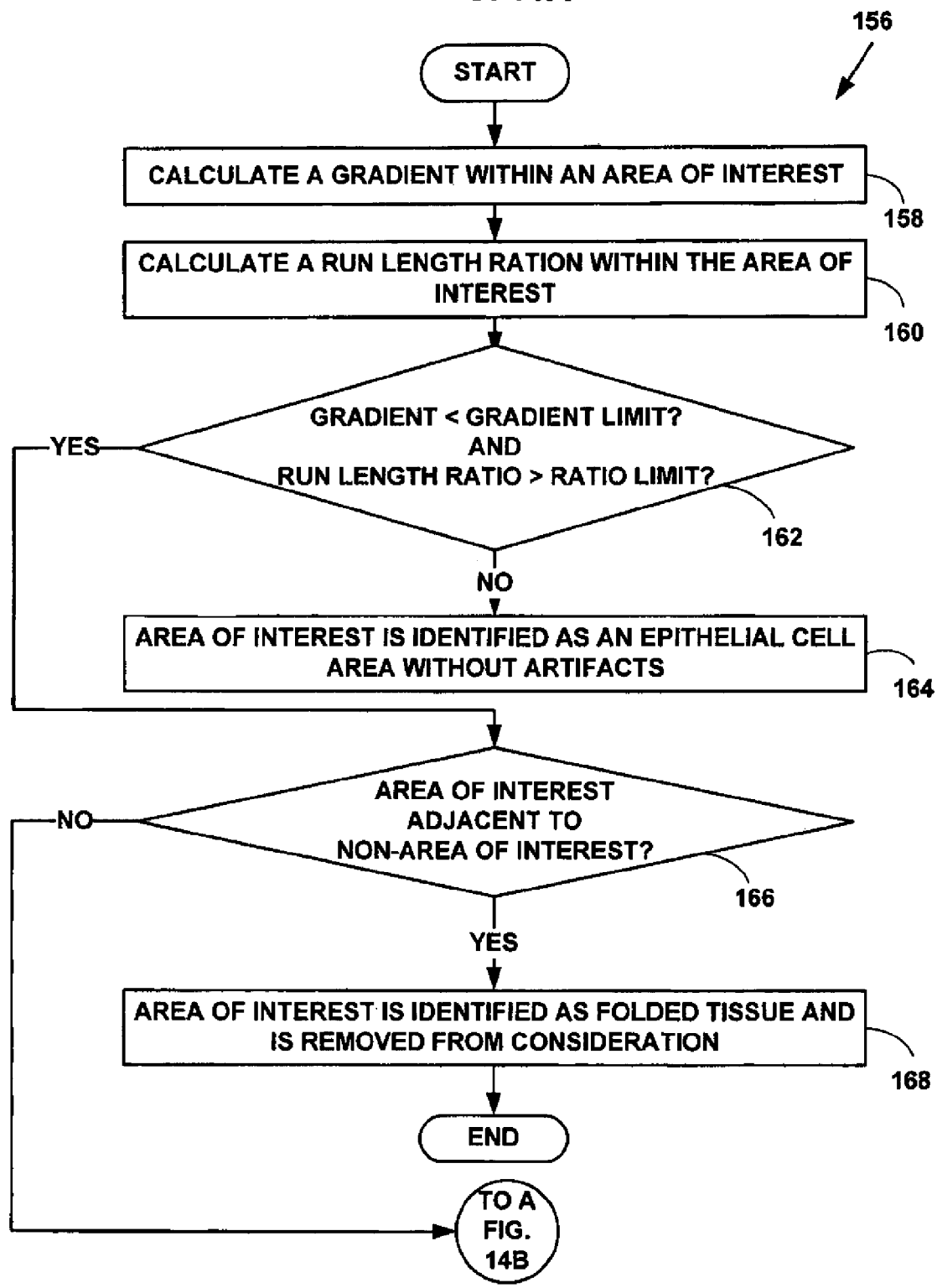

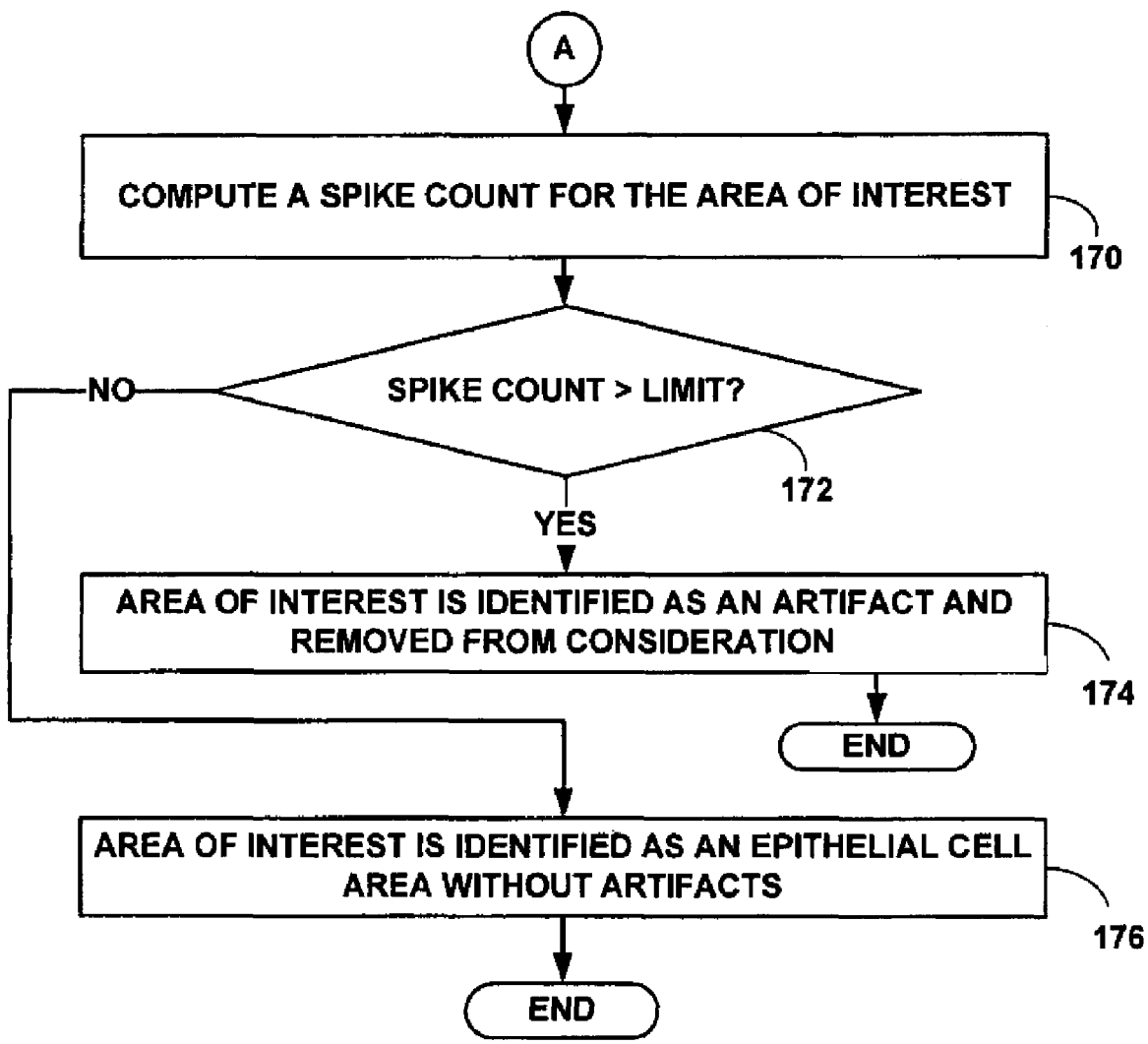

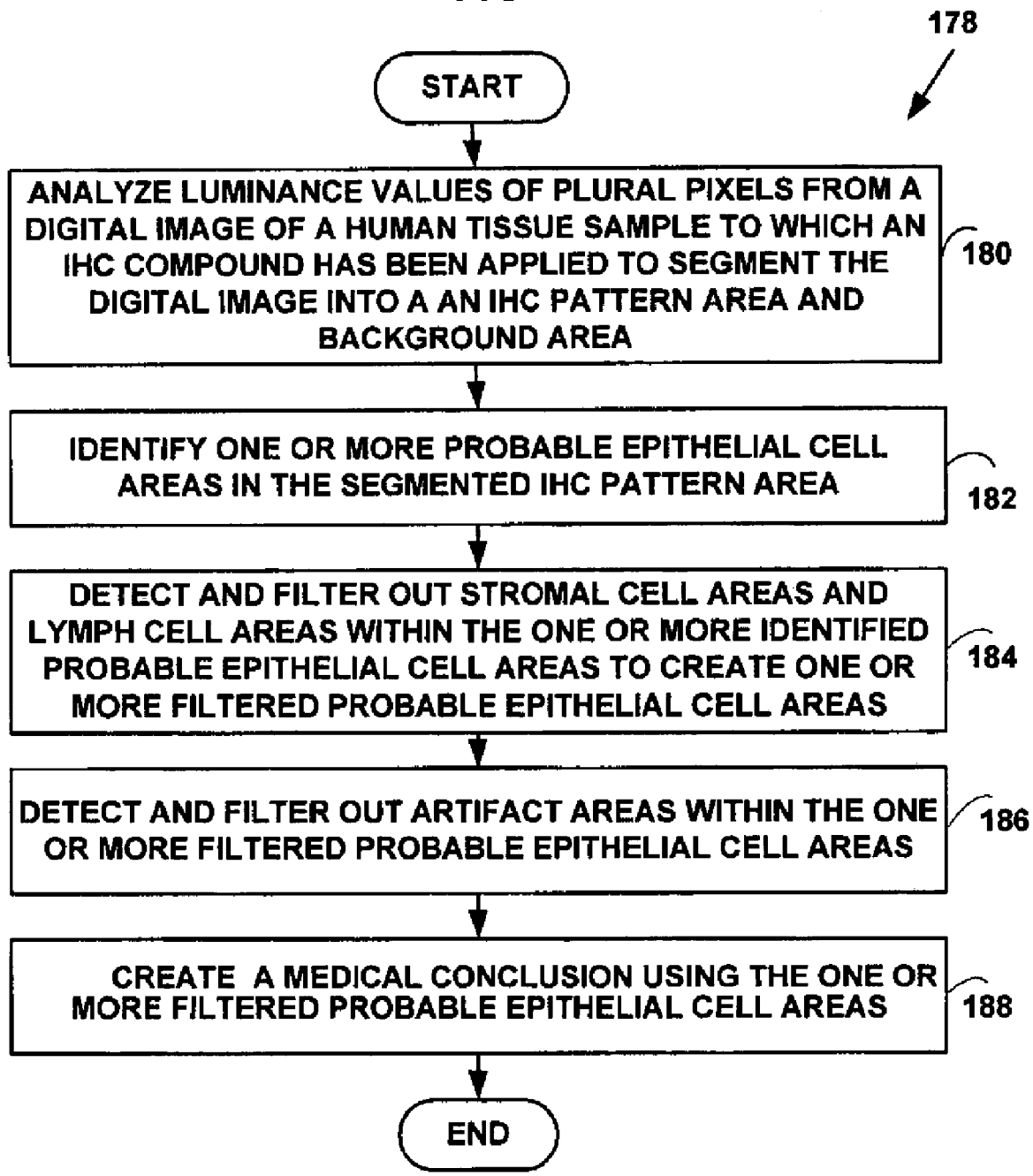

190

192
194

198
196

202
200

METHOD AND SYSTEM FOR AUTOMATED DETECTION OF IMMUNOHISTOCHEMICAL (IHC) PATTERNS

CROSS REFERENCES TO RELATED APPLICATIONS

This application claims priority to U.S. Provisional Patent Application No. 60/556,844, filed Mar. 27, 2004, the contents of which are incorporated by reference. This application is a continuation-in-part application of U.S. patent application Ser. No. 10/938,314, filed Sep. 10, 2004, which claims priority to U.S. Provisional Patent Application No. 60/501,412, filed Sep. 10, 2003, and U.S. Provisional Patent Application No. 60/515,582, filed Oct. 30, 2003, and this application is also a continuation-in-part of priority to U.S. patent application Ser. No. 10/966,071, filed Oct. 15, 2004, now abandoned which claims priority to U.S. Provisional Patent Application No. 60/530,174, filed Dec. 15, 2003, the contents of which are incorporated herein by reference in their entirety.

COPYRIGHT NOTICE

Pursuant to 37 C.F.R. 1.71(e), applicants note that a portion of this disclosure contains material that is subject to and for which is claimed copyright protection, such as, but not limited to, digital photographs, screen shots, user interfaces, or any other aspects of this submission for which copyright protection is or may be available in any jurisdiction. The copyright owner has no objection to the facsimile reproduction by anyone of the patent document or patent disclosure, as it appears in the Patent and Trademark Office patent file or records. All other rights are reserved, and all other reproduction, distribution, creation of derivative works based on the contents, public display, and public performance of the application or any part thereof are prohibited by applicable copyright law.

FIELD OF THE INVENTION

This invention relates to digital image processing. More specifically, it relates to a method and system for automated detection of immunohistochemical patterns.

BACKGROUND OF THE INVENTION

Pathology is a very visual science. For example, cancers grow in recognizable patterns that allow for their automated identification. A melanoma has a certain growth pattern that differs from a carcinoma of the prostate. Benign conditions also have patterns. Skin rashes, for example, are diagnosed by a combination of a type of inflammatory cells and location in the skin, that is, whether the inflammation is around blood vessels, within the epidermis, scattered, etc.

A fundamental aspect of histopathology has been the recognition that a morphological appearance of tumor can be correlated with degree of malignancy. Essentially pathology involves manual pattern recognition by human pathologists. This art of pattern recognition becomes very accurate after many years of practice. These basic principles of pattern recognition are extrapolated to all tissue types and in the detection of all pathological conditions. Pathological reports generated on the given sample must be clear and comprehensible to avoid medical errors. However, there is a high degree of inter-laboratory variability in the interpretation of what is seen and perceived by pathologists through manual microscopy. One of the reasons for this inter-laboratory variability is human error, which in turn points at lack of automation tools.

Use of automation tools in the pathological analysis helps reduce the variability that is often seen between different pathological laboratories.

As is known in the medical arts, diagnosis of cancer is done primarily on the basis of histologic (i.e., tissue) evaluation. Cancer identification is possible because of differential staining of tissue samples achieved by specific methods of staining such as Haematoxylin and Eosin (H/E) staining. However, for the specific diagnosis of the given type of cancer, a number of immunohistochemical (IHC) markers are used.

Estrogen plays a central role in regulating growth kinetics of a variety of epithelial linings, most importantly in the breast and endometrium. Estrogen binds to an estrogen receptor (ER), directly stimulating proliferation and differentiation. ER translocates to a cell nucleus, where it can bind to promoter sites and thus, regulates the expression of many other genes.

Estrogen also mediates part of its proliferative action on normal breast through transactivation of the progesterone receptor (PR); progesterone is also a mitogenic stimulus for mammary epithelium.

The assessment of ER and PR status in tumors by IHC has become the standard of care in breast cancers, and is rapidly being incorporated as a biomarker for other tumors as well. This analysis provides clinicians with important prognostic information, and helps predict the response to endocrine therapy.

For example, breast cancer patients whose lesions contain both ER and PR have the best probability of remission following hormonal therapy (approaching 70%) than the group of patients whose lesions contain either receptor alone (approximately 30%), or very low levels of both receptors (approximately 10%). It has been shown that tumors expressing ER and PR tend to be better differentiated and low-grade tumors, but this is not always the case. Cancer related survival in breast cancers is independently predicted by the status of ER and PR in some studies. Similarly, in the endometrium, ER negative status has been shown to be predictive of recurrence of low stage tumors, independent of tumor grade, while negative PR status is associated with a significant risk of lymph node metastasis independent of other clinicopathologic factors.

The proto-oncogene Her-2/neu (C-erbB2) has been localized to chromosome 17q and encodes a transmembrane tyrosine kinase growth factor receptor. The protein product of the Her-2/neu gene is overexpressed in 25-30% of breast cancers, and in approximately 90-95% of these cases, upregulation is a direct result of gene amplification.

A significant proportion of intraductal breast carcinomas (DCIS) demonstrate Her-2/neu amplification/overexpression, suggesting that this oncogene is activated early in the progression of malignant breast disease. Clinical studies in thousands of patients with breast cancer over the last decade have convincingly demonstrated that amplification/overexpression of Her-2/neu is associated with a poor prognosis. Additional solid tumors with amplification/overexpression of Her-2/neu include gynecologic malignancies (ovary and endometrium), and prostatic, pancreatic and hepatocellular adenocarcinomas; most studies in these malignancies also support the notion that increased Her-2/neu levels are associated with an adverse prognosis.

Cancers of the epithelial cells are the most common cancers, about 90% of the total cancers diagnosed. Therefore, identification of epithelial cells in a given digital image is a first step towards an actual identification of a cancer marker being searched for. For example, identification of ER/PR, Her2, or other markers in the breast cancer tissues. In breast cancer tissues, one specific marker searched for is ER/PR, present only in epithelial cells. Thus, a first step is to identify an epithelial part of a tissue sample. A pathologist, because of years of experience immediately differentiates an epithelial part of a tissue sample from a stromal part and looks for a specific marker. However, for a method to work on identification of a specific marker in the given tissue, it is essential to identify and differentiate the epithelial cell areas from the non-epithelial cell areas.

The importance of differentiating epithelial cell areas in a digital has multiple applications. Apart from identifying a cancer, it is critical to distinguish invasive carcinomas (IC) from noninvasive lesions. Since, cancer is life threatening when it becomes invasive, it carries a potential for spreading and metastasis. Therefore an accurate diagnosis of a presence, or absence of stromal invasion is essential.

Identification of the epithelial cell areas of a given digital image is a first step towards an automation of an entire pathological analysis through microscopy and would help in the applications such as, Nuclear pleomorphism. Mitotic Count, Tubule formation, Detection of markers stained by IHC, etc.

Using nuclear pleomorphism, manual grading of cancer comprises a very important part of the pathological analysis of cancer tissue. Cancers of the same organ could be of different types, but need to be assigned an overall grade. The results have to be accurate as it decides the prognosis and treatment of the patient. For example, breast cancer is classified on the basis of TNM system, the basis of which is a Nottingham modification of the Bloom and Richardson method of grading. The three separate parameters of this system are, Nuclear grade, Tubule formation, Mitosis.

Nuclear grade is assigned on the basis of appearance of the nucleus, its size, shape, appearance of nucleoli. Detection of nuclear pleomorphism and nucleus identification is essentially helpful in assigning a score in grading of breast cancer.

Tubule formation is checked in an entire image and differentiation of epithelial parts is helpful in assigning grades. Another important score of the grading system is the evaluation of Mitotic index of the sample. Several studies have shown that the mitotic count is the most important variable in the grading system used for the prognosis of breast cancer.

Accuracy of a detection of mitotic count is also essential. An overall grade of the neoplasm is determined by adding individual scores of the three separate parameters, tubules, nuclei and mitoses. The grading of the neoplasm has a very important role to play in the treatment and prognosis of the patient. All these parameters are searched for in epithelial cancer cells in the given image.

IHC markers, such as ER-PR quantitation is also used. In many areas of histopathology, just a broad category, such as a diagnosis of breast carcinoma, does not give enough information for the referring clinician to make decisions about patient prognosis and treatment. There are many IHC markers such as ER/PR, Her2, etc. which play a very important role in the accurate diagnosis of the cancer. For example, ER/PR assessment is important to ensure the appropriate use of hormonal therapies. It is also necessary to combine intensity staining measurement and object counting to precisely quantitative the percentage of positivity stained nuclei in the epithelial part of the tissue section.

Pathologists use their knowledge and expertise in identifying IHC patterns. Many of these properties do not have a rigid definition. Many a times pathologists give experience based decisions. However as mentioned earlier, there are several pitfalls and human error also contributes to the errors in the determination of epithelial cell count in IHC patterns.

It is observed that the seemingly simple task of epithelial cell counting becomes difficult because the counting has to be done for large number of sections. Non stained epithelial cells are difficult to identify in large IHC pattern. Problem gets even more complex if there are lymph cells of approximately same size as epithelial cell, or if some of the epithelial cells have vesicular structure. Even experienced pathologist might find it extremely difficult to count epithelial cells in a large IHC pattern.

Examination of tissue images typically has been performed manually by either a lab technician or a pathologist. In the manual method, a slide prepared with a biological sample is viewed at a low magnification under an optical microscope to visually locate IHC patterns of interest. Those areas of the slide where IHC patterns of interest are located are then viewed at a higher magnification to count epithelial cells.

An automated system that automatically analyzes digital images to which an IHC compound has been applied is expected to behave in a manner similar to human pathologist and at the same time produce consistent conclusions and/or better, conclusions with fewer errors than human pathologists.

However, there are several problems associated with using existing digital image analysis techniques for analyzing images for identifying epithelial cells in IHC patterns. One problem is that existing digital image analysis uses aggregate values over IHC patterns rather than individual epithelial cell level. Another problem is identification of IHC pattern boundaries. Standard digital image analysis based on texture alone does not provide accurate boundaries of IHC patterns. There is a need to incorporate some of the IHC properties of biological tissues in identifying accurate boundaries.

There have been attempts to solve some of the problems associated with automating manual methods for analyzing IHC samples. Automated analysis systems have been developed to improve the speed and accuracy of the IHC testing process. For example, U.S. Pat. No. 6,546,123, entitled "Automated detection of objects in a biological sample" that issued to McLaren, et al. teaches "a method, system, and apparatus are provided for automated light microscopic for detection of proteins associated with cell proliferative disorders."

U.S. Pat. No. 5,546,323, entitled "Methods and apparatus for measuring tissue section thickness," that issued to Bacus et al., teaches "an apparatus and method for measuring the thickness of a tissue section with an automated image analysis system, preferably using polyploid nuclear DNA content, for subsequent use in analyzing cell objects of a specimen cell sample for the diagnosis and treatment of actual or suspected cancer or monitoring any variation in the nominal thickness in a microtome setting. An image of a measurement material, such as a rat liver tissue section, having known cell object attributes is first digitized and the morphological attributes, including area and DNA mass of the cell objects, are automatically measured from the digitized image. The measured attributes are compared to ranges of attribute values which are preestablished to select particular cell objects. After the selection of the cell objects, the operator may review the automatically selected cell objects and accept or change the measured cell object attribute values. In a preferred embodiment, each selected cell object is assigned to one of three classes corresponding to diploid, tetraploid and octoploid cell morphology and the measured DNA mass of the identified cell object fragments in the rat liver tissue section sample may be corrected. Next, the selected cell objects of the measurement material, e.g., DNA Mass, are then graphically displayed in a histogram and the thickness of the rat liver tissue section can be measured based upon the distribution."

U.S. Pat. No. 5,526,258, entitled "Method and apparatus for automated analysis of biological specimens," that issued to Bacus teaches "an apparatus and method for analyzing the cell objects of a cell sample for the diagnosis and treatment of actual or suspected cancer is disclosed. An image of the cell sample is first digitized and morphological attributes, including area and DNA mass of the cell objects are automatically measured from the digitized image. The measured attributes are compared to ranges of attribute values which are preestablished to select particular cell objects having value in cancer analysis. After the selection of cell objects, the image is displayed to an operator and indicia of selection is displayed with each selected cell object. The operator then reviews the automatically selected cell objects, with the benefit of the measured cell object attribute values and accepts or changes the automatic selection of cell objects. In a preferred embodiment, each selected cell object is assigned to one of six classes and the indicia of selection consists of indicia of the class into which the associated cell object has been placed. The measured DNA mass of identified cell object fragments in tissue section samples may also be increased to represent the DNA mass of the whole cell object from which the fragment was sectioned.

U.S. Pat. No. 5,018,209, entitled "Analysis method and apparatus for biological specimens," that issued to Bacus et al., teaches "a method and apparatus are provided for selecting and analyzing a subpopulation of cells or cell objects for a certain parameter such as DNA, estrogen, and then measuring the selected cells. The observer in real time views a field of cells and then gates for selection based on the morphological criteria those cells that have the visual parameter such as colored DNA or colored antigen into a subpopulation that is to be measured. The selected cells are examined by digital image processing and are measured for a parameter such as a true actual measurement of DNA in picograms. A quantitation of the measured parameter is generated and provided."

U.S. Published Patent Application, 20030049701, entitled "Oncology tissue microarrays," published by Muraca suggests "oncology tissue microarrays. In one aspect, the microarrays comprise a plurality of cell and/or tissue samples, each sample representing a different type of cancer. In another aspect of the invention, each sample represents a different stage of cancer. In still a further aspect of the invention, samples are ordered on the substrate of the microarray into groups according to common characteristics of the patients from whom the samples are obtained. By dividing tissue samples on the substrate into different groupings representing different tissue types, subtypes, histological lesions, and clinical subgroups, the microarrays according to the invention enable ultra-high-throughput molecular profiling."

U.S. Published Patent Application, 20030092047, entitled "Methods of cytodiagnostic staging of neoplasia and squamous cell carcinoma," published by LaMorte suggests "Methods of diagnosing whether an epithelial tissue is an abnormal tissue by determining an expression pattern for PML in the epithelial tissue; determining an expression pattern for nuclear bodies in the epithelial tissue; determining SUMO-1 colocalization and comparing the expression pattern for PML and the expression pattern for nuclear bodies with a control are disclosed. Also disclosed are methods for diagnosing whether a subject has mild dysplasia, moderate dysplasia, Type A severe dysplasia, Type B severe dysplasia, cervical squamous cell carcinoma, or poorly-differentiated cervical squamous cell carcinoma by determining an expression pattern for PML in an epithelial tissue sample from the subject; determining an expression pattern for nuclear bodies in the epithelial tissue; determining SUMO-1 colocalization; and determining whether the expression pattern for PML, the expression pattern for nuclear bodies, and the SUMO-1 colocalization of the epithelial tissue sample is consistent with expression patterns expected for mild dysplasia, moderate dysplasia, Type A severe dysplasia, Type B severe dysplasia, cervical squamous cell carcinoma, or poorly-differentiated cervical squamous cell carcinoma."

U.S. Published Patent Application, 20030170703, entitled "Method and/or system for analyzing biological samples using a computer system," published by Piper et al. suggests "a method and/or system for making determinations regarding samples from biologic sources. A computer implemented method and/or system can be used to automate parts of the analysis."

Biogenex has reported products for image analysis for diagnosis and screening purposes where morphometry has been used in numerous research studies to differentiate a variety of neoplastic and non-neoplastic conditions. Cells or other structures of diagnostic interest are measured using image analysis techniques.

The ChromaVision Automated Cellular Imaging System (ACIS) provides automated measurements on immunohistochemically (IHC) stained tissue sections.

Applied Imaging Reasearch provides automated quantification of IHC stained tissue sections.

However, these systems still do not solve all of the problems associated with automatically analyzing digital images of tissue samples to which an IHC compound has been applied.

Therefore it is desirable to provide an automation tool that can clearly differentiate an epithelial part form the non-epithelial part of digital images of tissue samples to which an IHC compound has been applied.

SUMMARY OF THE INVENTION

In accordance with preferred embodiments of the present invention, some of the problems associated with automated biological sample analysis systems are overcome. A method and system for automated detection of immunohistochemical (IHC) patterns is presented.

The method and system is able to automatically differentiate an epithelial cell part from a non-epithelial cell part of a digital image of a tissue sample to which an IHC compound has been applied. The method and system may improve the prognosis and selection of appropriate therapy and prediction of therapeutic outcome of diseases such as human cancers.

The foregoing and other features and advantages of preferred embodiments of the present invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein:

FIG. 7 is a flow diagram illustrating a method for segmentation of digital images to determine plural cells of interest in the enhanced digital image;

FIG. 8 is a block diagram of exemplary neighborhood masks used with convex hulls;

FIGS. 9A and 9B are flow diagram illustrating a method for detecting epithelial cell areas from connected components identified with a method of FIG. 7;

FIGS. 11A and 11B are a flow diagram illustrating an exemplary method for removing artificats;

FIG. 12 is a flow diagram illustrating a method for automated digital image analysis for identifying epithelial cell areas in IHC patterns;

DETAILED DESCRIPTION OF THE INVENTION

Exemplary Epithelial Analysis System

Figure 1:
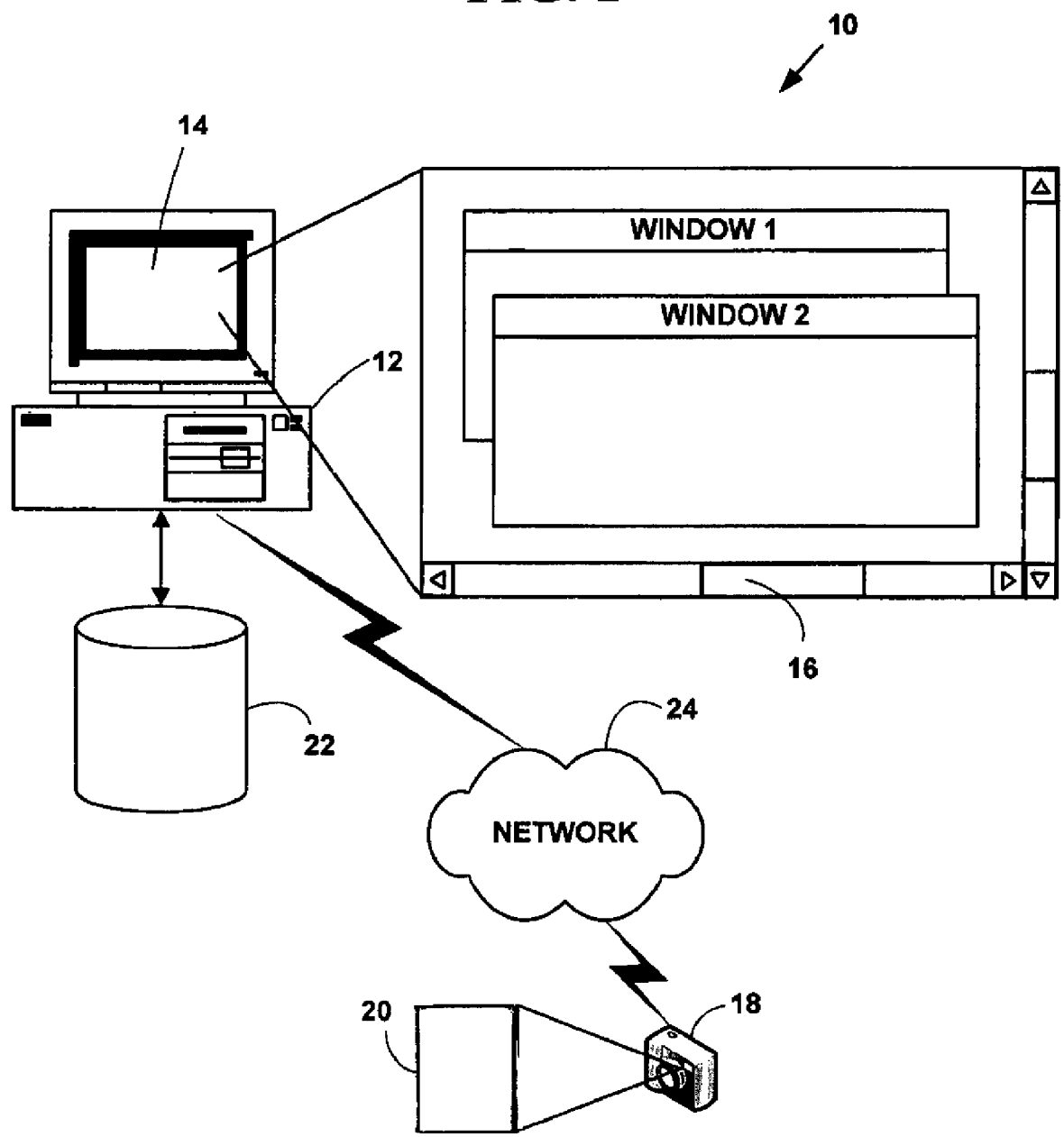
FIG. 1 is a block diagram illustrating an exemplary automated digital image based epithelial detection and classification system.
Figure 2:
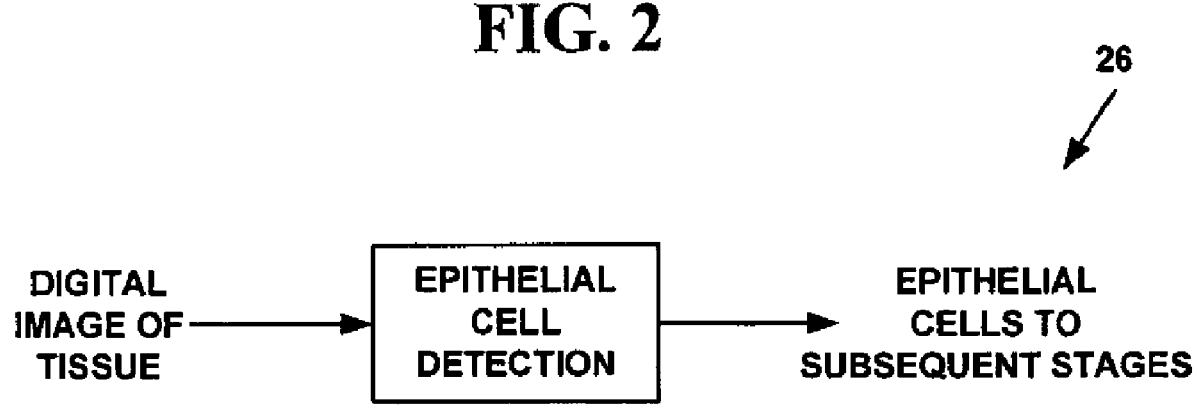
FIG. 2 is a block diagram illustrating an exemplary epithelial cell filter.

FIG. 1 is a block diagram illustrating an exemplary automated digital image based epithelial detection and classification system 10. The exemplary system 10 includes one or more computers 12 with a computer display 14 (one of which is illustrated). The computer display 14 presents a windowed graphical user interface ("GUI") 16 with multiple windows to a user. The system 10 may optionally include a microscope or other magnifying device (not illustrated in FIG. 1). The system 10 further includes a digital camera 18 (or analog camera) used to provide plural digital images 20 in various digital images or digital data formats. One or more databases 22 (one or which is illustrated) include biological sample information in various digital images or digital data formats. The databases 22 may be integral to a memory system on the computer 12 or in secondary storage such as a hard disk, floppy disk, optical disk, or other non-volatile mass storage devices. The computer 12 and the databases 22 may also be connected to an accessible via one or more communications networks 24.

The one or more computers 12 may be replaced with client terminals in communications with one or more servers, or with personal digital/data assistants (PDA), laptop computers, mobile computers, Internet appliances, one or two-way pagers, mobile phones, or other similar desktop, mobile or hand-held electronic devices.

The communications network 24 includes, but is not limited to, the Internet, an intranet, a wired Local Area Network (LAN), a wireless LAN (WiLAN), a Wide Area Network (WAN), a Metropolitan Area Network (MAN), Public Switched Telephone Network (PSTN) and other types of communications networks 24.

The communications network 24 may include one or more gateways, routers, or bridges. As is known in the art, a gateway connects computer networks using different network protocols and/or operating at different transmission capacities. A router receives transmitted messages and forwards them to their correct destinations over the most efficient available route. A bridge is a device that connects networks using the same communications protocols so that information can be passed from one network device to another.

The communications network 24 may include one or more servers and one or more web-sites accessible by users to send and receive information useable by the one or more computers 12. The one ore more servers, may also include one or more associated databases for storing electronic information.

The communications network 24 includes, but is not limited to, data networks using the Transmission Control Protocol (TCP), User Datagram Protocol (UDP), Internet Protocol (IP) and other data protocols.

As is know in the art, TCP provides a connection-oriented, end-to-end reliable protocol designed to fit into a layered hierarchy of protocols which support multi-network applications. TCP provides for reliable inter-process communication between pairs of processes in network devices attached to distinct but interconnected networks. For more information on TCP see Internet Engineering Task Force (ITEF) Request For Comments (RFC)-793, the contents of which are incorporated herein by reference.

As is know in the art, UDP provides a connectionless mode of communications with datagrams in an interconnected set of computer networks. UDP provides a transaction oriented datagram protocol, where delivery and duplicate packet protection are not guaranteed. For more information on UDP see IETF RFC-768, the contents of which incorporated herein by reference.

As is known in the art, IP is an addressing protocol designed to route traffic within a network or between networks. IP is described in IETF Request For Comments (RFC)-791, the contents of which are incorporated herein by reference. However, more fewer or other protocols can also be used on the communications network 19 and the present invention is not limited to TCP/UDP/IP.

The one or more database 22 include plural digital images 20 of biological samples taken with a camera such as a digital camera and stored in a variety of digital image formats including, bit-mapped, joint pictures expert group (JPEG), graphics interchange format (GIF), etc. However, the present invention is not limited to these digital image formats and other digital image or digital data formats can also be used to practice the invention.

The digital images 20 are typically obtained by magnifying the biological samples with a microscope or other magnifying device and capturing a digital image of the magnified biological sample (e.g., groupings of plural magnified cells, etc.).

An operating environment for the devices of the exemplary system 10 include a processing system with one or more high speed Central Processing Unit(s) ("CPU"), processors and one or more memories. In accordance with the practices of persons skilled in the art of computer programming, the present invention is described below with reference to acts and symbolic representations of operations or instructions that are performed by the processing system, unless indicated otherwise. Such acts and operations or instructions are referred to as being "computer-executed," "CPU-executed," or "processor-executed."

It will be appreciated that acts and symbolically represented operations or instructions include the manipulation of electrical signals by the CPU or processor. An electrical system represents data bits which cause a resulting transformation or reduction of the electrical signals or biological signals, and the maintenance of data bits at memory locations in a memory system to thereby reconfigure or otherwise alter the CPU's or processor's operation, as well as other processing of signals. The memory locations where data bits are maintained are physical locations that have particular electrical, magnetic, optical, or organic properties corresponding to the data bits.

The data bits may also be maintained on a computer readable medium including magnetic disks, optical disks, organic memory, and any other volatile (e.g., Random Access Memory ("RAM")) or non-volatile (e.g., Read-Only Memory ("ROM"), flash memory, etc.) mass storage system readable by the CPU. The computer readable medium includes cooperating or interconnected computer readable medium, which exist exclusively on the processing system or can be distributed among multiple interconnected processing systems that may be local or remote to the processing system.

The term "sample" includes cellular material derived from a biological organism. Such samples include but are not limited to hair, skin samples, tissue samples, cultured cells, cultured cell media, and biological fluids. The term "tissue" refers to a mass of connected cells (e.g., central nervous system (CNS) tissue, neural tissue, or eye tissue) derived from a human or other animal and includes the connecting material and the liquid material in association with the cells. The term "biological fluid" refers to liquid material derived from a human or other animal. Such biological fluids include, but are not limited to, blood, plasma, serum, serum derivatives, bile, phlegm, saliva, sweat, amniotic fluid, and cerebrospinal fluid (CSF), such as lumbar or ventricular CSF. The term "sample" also includes media containing isolated cells. One skilled in the art may determine the quantity of sample required to obtain a reaction by standard laboratory techniques. The optimal quantity of sample may be determined by serial dilution.

The term "biological component" include, but not limited to nucleus, cytoplasm, membrane, epithelium, nucleolus and stromal. The term "medical diagnosis" includes analysis and interpretation of the state of tissue material in a biological fluid. The interpretation includes classification of tissue sample as "benign tumor cell" or "malignant tumor cell". Interpretation also includes quantification of malignancy.

Digital Images

A digital image 20 typically includes an array, usually a rectangular matrix, of pixels. Each "pixel" is one picture element and is a digital quantity that is a value that represents some property of the image at a location in the array corresponding to a particular location in the image. Typically, in continuous tone black and white images the pixel values represent a gray scale value.

Pixel values for a digital image 20 typically conform to a specified range. For example, each array element may be one byte (i.e., eight bits). With one-byte pixels, pixel values range from zero to 255. In a gray scale image a 255 may represent absolute white and zero total black (or visa-versa).

Color images consist of three color planes, generally corresponding to red, green, and blue (RGB). For a particular pixel, there is one value for each of these color planes, (i.e., a value representing the red component, a value representing the green component, and a value representing the blue component). By varying the intensity of these three components, all colors in the color spectrum typically may be created.

However, many images do not have pixel values that make effective use of the full dynamic range of pixel values available on an output device. For example, in the eight-bit or byte case, a particular image may in its digital form only contain pixel values ranging from 100 to 150 (i.e., the pixels fall somewhere in the middle of the gray scale). Similarly, an eight-bit color image may also have RGB values that fall within a range somewhere in middle of the range available for the output device. The result in either case is that the output is relatively dull in appearance.

The visual appearance of an image can often be improved by remapping the pixel values to take advantage of the full range of possible outputs. That procedure is called "contrast enhancement." While many two-dimensional images can be viewed with the naked eye for simple analysis, many other two-dimensional images must be carefully examined and analyzed. One of the most commonly examined/analyzed two-dimensional images is acquired using a digital camera connected to an optical microscope.

One type of commonly examined two-dimensional digital images 20 are digital images made from biological samples including cells, tissue samples, etc. Such digital images are commonly used to analyze biological samples including a determination of certain know medical conditions for humans and animals. For example, digital images are used to determine cell proliferate disorders such as cancers, etc. in humans and animals.

Digital images 20 captured through optical microscopes represent the images seen by a human eye through the microscope. However, a pathologist can easily identify and distinguish between various phases of mitotic cells and non-mitotic cells, even though there are variations in staining, variations in illumination across a slide or the presence of a mask or an artifact. This is because of experience and knowledge of the domain of the pathologist.

Identification of Epithelial Regions

The identification of the epithelial regions of a digital image 20 of a tissue sample is a first step towards the automation of the entire pathological analysis through microscopy and assists in the applications illustrated in Table 1.

TABLE 1

Nuclear pleomorphism
Mitotic Count
Tubule formation
Detection of markers stained by IHC
Detection of markers stained by immunofluorescence Grading of cancer cells comprises a very important part of the pathological analysis of cancer tissue. Cancers of the same organ could be of different types, but still need to be assigned an overall grade. The results have to be accurate as it decides the prognosis and treatment of the patient. For example, breast cancer is classified on the basis of TNM system, the basis of which is a Nottingham modification of the Bloom and Richardson method of grading. The three separate parameters of this system are listed in Table 2.

TABLE 2

Nuclear grade
Tubule formation
Mitosis

"Nuclear grade" is assigned on the basis of appearance of the nucleus, its size, shape, appearance of nucleoli. Detection of nuclear pleomorphism and nucleus identification is essentially helpful in assigning the score in grading of breast cancer. "Tubule formation" is checked in the entire image and differentiation of epithelial parts is helpful in assigning the grades. Another important score of the grading system is the evaluation of "Mitotic index" of the sample. Several studies have shown that the mitotic count is the most important variable in the grading system used for the prognosis of breast cancer. Accuracy of the detection of mitotic count is most essential. The overall grade of the neoplasm is determined by adding individual score of the three separate parameters, tubules, nuclei and mitoses. The grading of the neoplasm has a very important role to play in the treatment and prognosis of the patient. All these parameters are looked for in epithelial cancer cells in a digital image 20.

Immunohistochemical (IHC) Markers

In many areas of histopathology, just a broad category, such as a diagnosis of breast carcinoma, does not give enough information for the referring clinician to make decisions about patient prognosis and treatment. There are many IHC markers such as ER/PR, Her2, etc. which play a very important role in the accurate diagnosis of the cancer. It is necessary to combine intensity staining measurement and object counting to precisely quantitative the percentage of positivity stained nuclei in an epithelial part of the tissue section.

Manually detecting epithelial cells has always been a challenging task. IHC patterns have a very complex structure and a pathologist can manually detect the different types of cells and their morphologies in digital image 20 allowing a medical diagnosis or prognosis to be determined. The present invention automatically detects an epithelial cell subpopulation in a digital image, in-situ.

Clearly differentiating an epithelial part from a non-epithelial part of a tissue sample in a digital image 20 helps reduce errors in automated analysis of a tissue sample. One of the first steps in providing an automated epithelial cell analysis method is to apply one or more different epithelial cell filters to detect all epithelial cells in a digital image 20.

Exemplary Automated Detection of Immunonhistochemical Patterns

Figure 3:
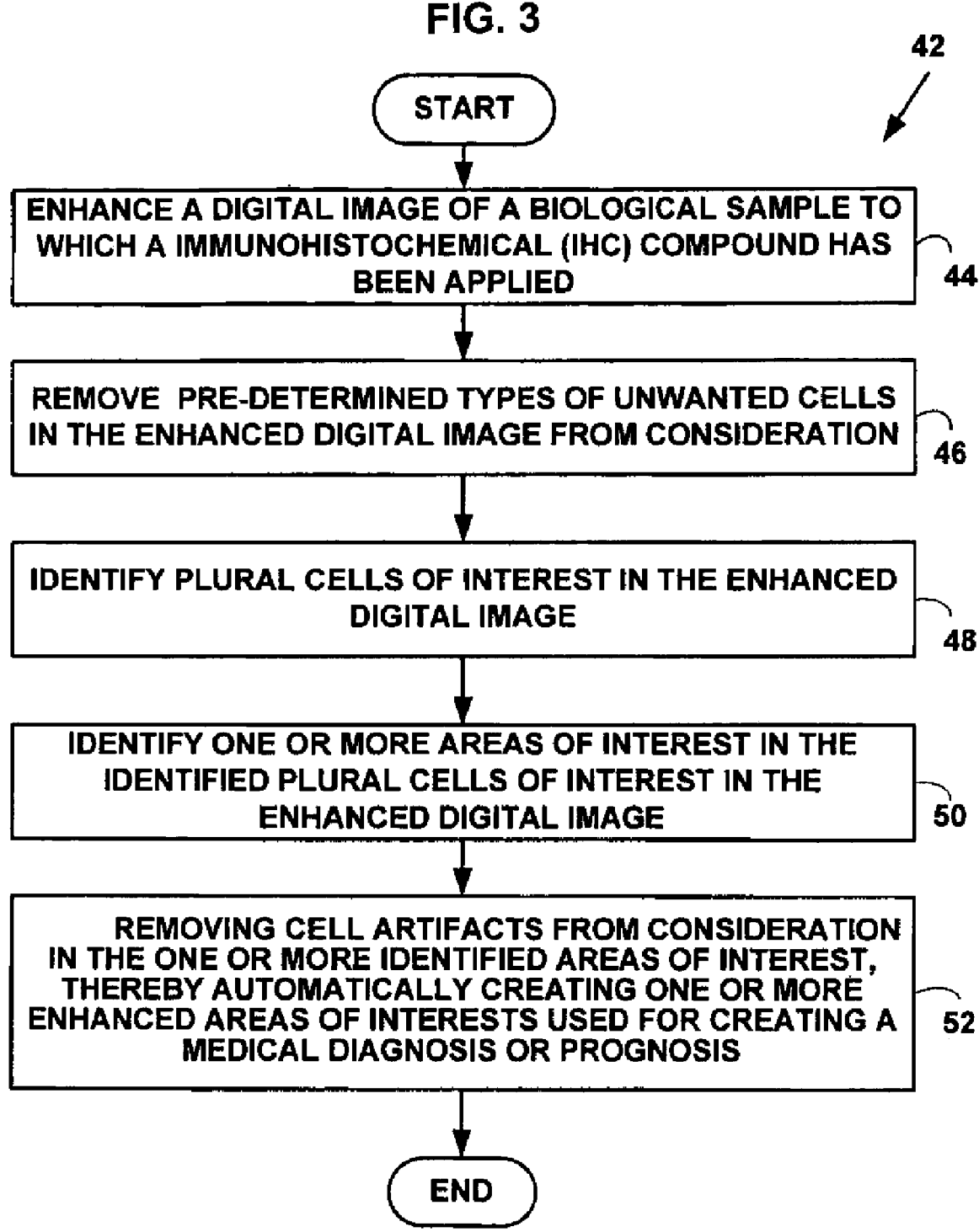
FIG. 3 is a flow diagram illustrating an exemplary automated method for detection of immunohistochemical patterns.

FIG. 3 is a flow diagram illustrating an exemplary Method 42 for automated detection of immunohistochemical (IHC) patterns. At Step 44, a digital image of a biological sample to which an IHC compound has been applied is enhanced. At Step 46, pre-determined types of unwanted cells in the enhanced digital image are removed from consideration. At Step 48, plural cells of interest in the enhanced digital image are identified. At Step 50, one or more areas of interest in the identified plural cells of interest in the enhanced digital image are identified. At step 52, cell artifacts from the one or more identified areas of interest are automatically removed from consideration, thereby creating one or more enhanced areas of interests used for creating a medical diagnosis or prognosis.

Method 42 is illustrated with one exemplary embodiment. However, the present invention is not limited to such an embodiment and other embodiments can also be used to practice the invention.

In such an exemplary embodiment, at Step 44, a contrast of a digital image 20 of a biological sample to which an IHC compound has been applied is enhanced. Digital images 20 captured through optical microscopes represent the images seen by a human eye through the microscope. However, a pathologist can easily identify and distinguish between epithelial 32, stromal 36 and lymph 38 cells, even though there are variations in staining, variations in illumination across a slide, the presence of a mask or an artifact 40, etc. This manual identification is possible because of the experience and knowledge of the pathology domain by the pathologist.

At Step 44, the same objective is automatically achieved by reducing the effect of variations in staining intensity, effect of color masks and other anomalies by: (1) verifying the content of a digital image 20; and (2) contrast modification of the digital image 20 based on image statistics. However, the present invention is not limited to these two techniques and other techniques can also be used to practice the invention at Step 44.

Verifying content of a digital image 20: A cell detection process can be simplified if processing fields or slides that do not have a tissue sample are eliminated from consideration. The content of a digital image 20 is detected by computing a mean and standard deviation of Red, Blue and Green planes of the digital image 20. In the case of images without a tissue sample, there will be little or no variations in colors. Standard deviation, which reflects variation will be low.

Contrast modification: "Contrast" in a digital image is referred to a difference in luminosity level between any two given pixels. Contrast could be in the same color plane or across color planes. In the current invention Red, Green and Blue color planes are considered. In the prior art, other color models like Hue Saturation and Intensity (HSI) are used. However, it is realized that pathologists use color information extensively. Further, the term Hue is interpreted by pathologists and image processing people differently. Therefore in the current invention RGB model is used. In another embodiment, HSI are used.

A digital image 20 is considered "high contrast" if its luminosity levels range from a minimum value (e.g., zero) to a maximum value (e.g., 255). In the case of low contrast images, this range could be as small as 50, for example, or range from 100 to 150. In the case of high contrast images, the pixels belonging to nuclei and mitotic cell look dark, cytoplasm looks moderate level and vacuoles will be of highest luminosity. Contrast modification helps improve low contrast images to aid automated analysis. Modification is used such that dark pixels become even darker and brighter pixels maintain at least a same level of initial brightness. Determining a minimum intensity in each color plane independently results in contrast enhancement in the active range of pixels in a digital image.

Color values at a given pixel are independently computed from Red, Green and Blue components of the digital image 20. A determination of an active range of original intensities in each of the colors is made by computing histograms of color planes (i.e., R, G and B) of the digital image 20. The histograms are used to compute a minimum intensity such that, starting from lowest intensity, cumulative pixels up to minimum intensity is equal to about 0.5% to 5% of a total number pixels in the digital image. An original active range is mapped to an enhanced range of intensity value (zero, 255). All pixels with value less than minimum intensity are also set to a value of zero. However, the present invention is not limited to this embodiment and other percentages and active ranges of intensities can also be used to practice the invention.

These histograms are used to compute a minimum intensity such that, starting from lowest intensity, the cumulative pixels up to minimum intensity is equal to pre-defined percentage "$P_{min}$," and a maximum intensity such that, starting from lowest intensity, the cumulative pixels up to maximum intensity is equal to a pre-defined percentage "$P_{max}$." Pixels in the active range, that is, in between minimum intensity and maximum intensity value are later mapped to an enhanced range (e.g., zero to 255). Equation (1) is used for modifying pixel intensities.

$$\text{Modified pixel intensity} = Con1 * (\text{Pixel Intensity} - P_{min})/(P_{max} - P_{min}), \tag{1}$$

where Con1 is a first constant with a maximum value in the enhanced range or 255. However, the present invention is not limited constant value and other constant values can also be used to practice the invention.

A pre-defined percentage of 2% is used for "$P_{min}$," for determining a minimum intensity in each color plane in the current embodiment. However, the present invention is not limited to such a pre-defined percentage and other pre-defined percentages can also be used to practice the invention.

A pre-defined percentage of 90% is used for "$P_{max}$," for determining a maximum intensity in each color plane in the current embodiment. However, the present invention is not limited to such a pre-defined percentage and other pre-defined percentages can also be used to practice the invention.

Areas of interest to be identified (Step 48) are based on at least two distinctive features of an epithelial area of cells. Epithelial areas are "darker" compared to stromal cells 34, and epithelial cells 30 are densely packed in epithelial area. A minimum background intensity is computed using a mean and standard deviation as is illustrated in Equation (2).

$$\text{Minimum background intensity}=M-(D/(\log(D)+\text{Con}1)), \quad (2)$$

where "M" is a mean, "D" is a standard deviation and "Con1" is a pre-determined constant (e.g., one). Minimum background intensity is computed independently for each color plane. If any color component of a pixel is greater than the respective minimum background intensity, then the pixel is treated as background pixel. All background pixels are set to a value of a maximum value (e.g., 255) in the Red, Green and Blue color planes.

Figure 6:
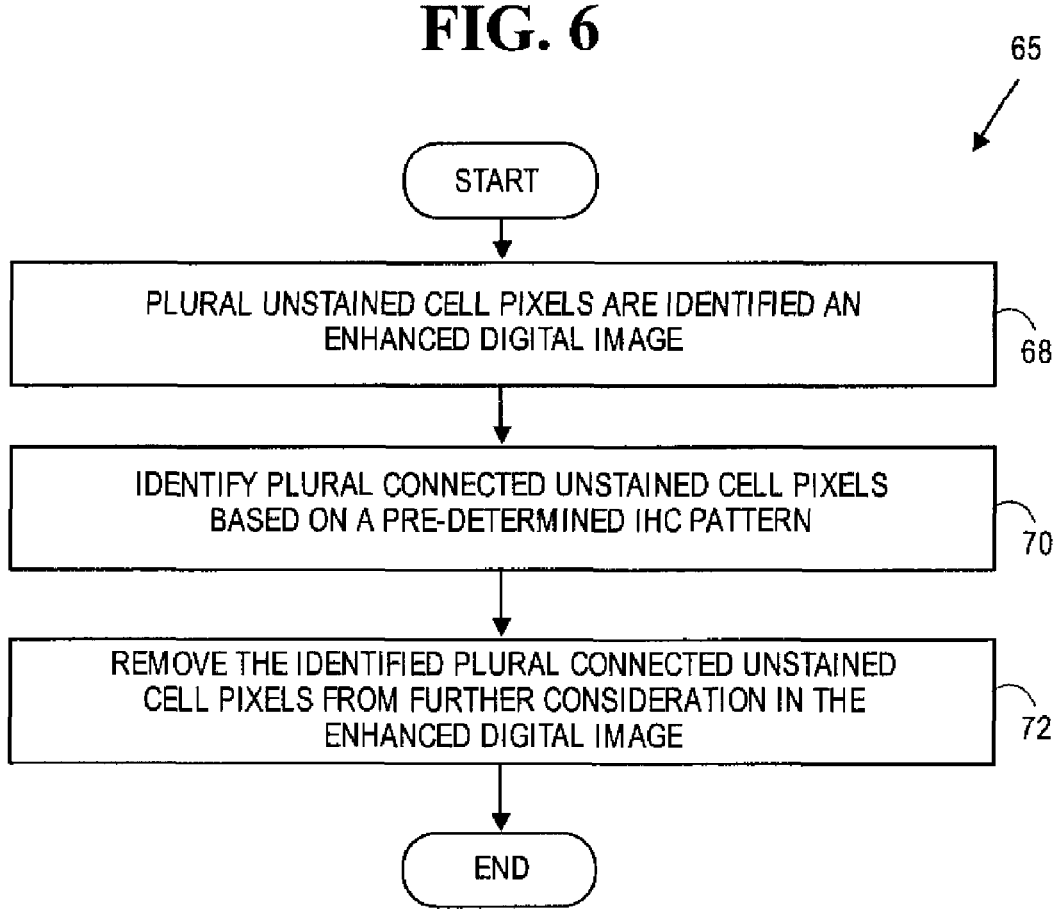
FIG. 6 is a flow diagram illustrating an exemplary method for segmentation of digital images to remove unwanted cells from consideration.

FIG. 6 is a flow diagram illustrating a Method 54 for digital image enhancement. In one embodiment, Method 54 is used at Step 44 of Method 42. However, the present invention is not limited to such an embodiment and other methods can also be used to practice the invention at Step 44.

Figure 4:
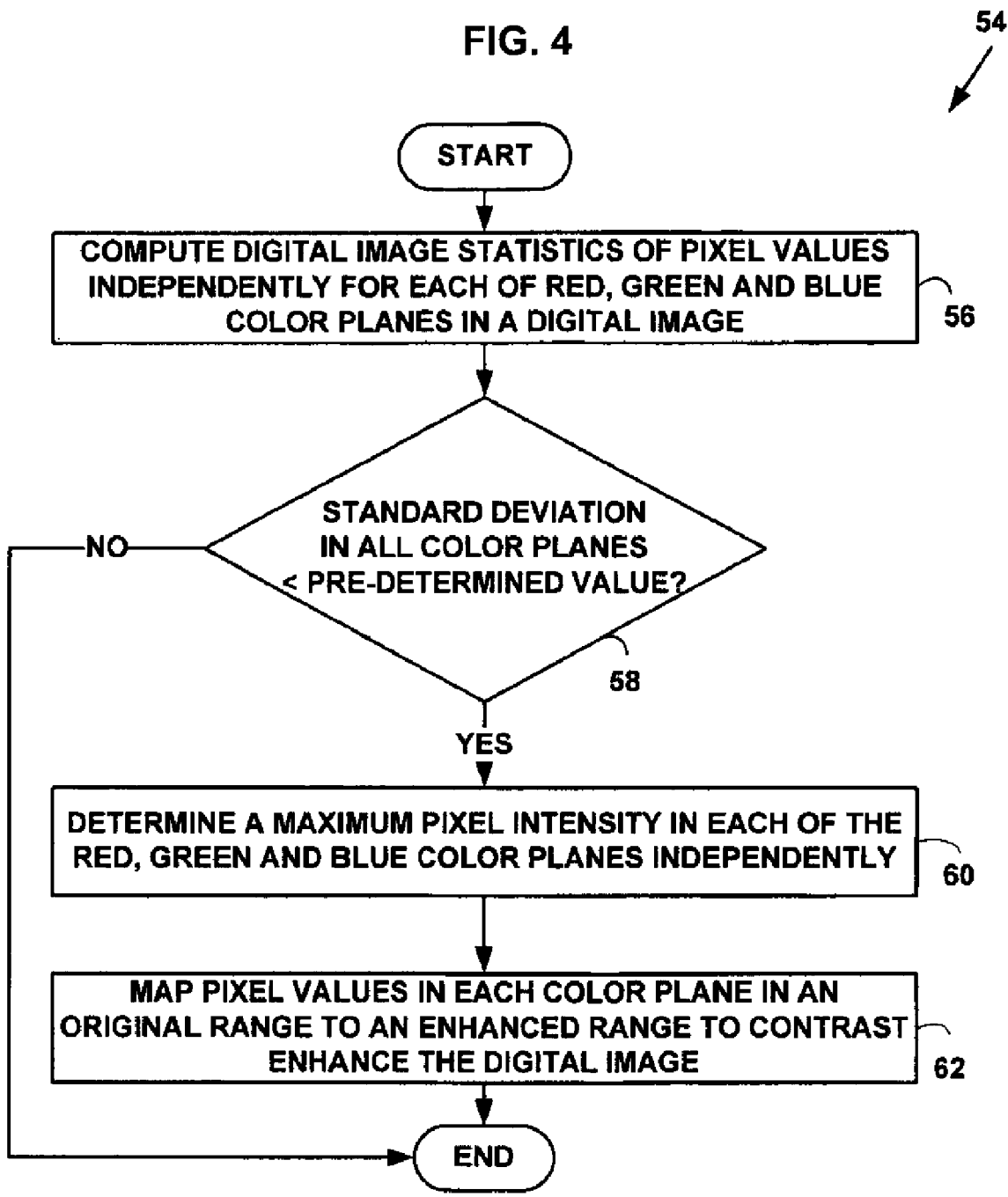
FIG. 4 is a flow diagram illustrating a method for digital image enhancement.

FIG. 4 is a flow diagram illustrating a Method 54 for digital image enhancement. In one embodiment, Method 54 is used at Step 44 of Method 42. However, the present invention is not limited to such an embodiment and other methods can also be used to practice the invention at Step 44.

In FIG. 3 at Step 56, digital image statistics of pixel values for each of Red, Green and Blue color planes in the digital image are computed independently. The digital image statistics include computing histograms and image statistics including mean and standard deviation for the Red, Green and Blue color planes independently. If there is a dominant color a standard deviation will be large. Therefore, a large standard deviation in all three color planes is considered to determine a presence of a color mask.

At Step 60, a "maximum intensity" of an original active intensity range is determined using a distribution of pixel values in the Red, Green and Blue color planes independently. In one embodiment, the distribution of pixel values includes considering about 95% of a total number of pixels in each color plane. However, the present invention is not limited to such an embodiment and other percentages can also be used to practice the invention.

At Step 62, pixel values in each color plane are mapped such that pixel values in an original intensity range {minimum intensity to maximum intensity} are mapped to an enhanced intensity range {zero to maximum intensity} (e.g., zero to 255) to contrast enhance the digital image 20.

Contrast enhancement or difference between pixels level is increased by setting all pixels below minimum intensity level to zero, keeping and keeping maximum intensity in each color plane the same.

Returning to FIG. 4 at Step 46, pre-determined types of unwanted cells in the enhanced digital image 20 are removed from consideration. In one embodiment, stromal cells 36 and/or lymph cells 38 are removed from consideration from the digital image 20 via segmenting. However, the present invention, is not limited to this embodiment and other types of unwanted cells can also be removed from the digital image.

In one embodiment, a Gaussian kernel is used to segment the enhanced digital image into plural objects. A Gaussian kernel is used for a weighted averaging of pixels in a small window centered around a given pixel to create a segment. Keeping a window size equal to a width of two typical epithelial cells 32, differentiation can be made between densely packed epithelial cell 32 areas and stromal cell 36 areas. Weighted averages are very large in stromal cell 36 areas and smaller in lymph cells 38.

Figure 5:
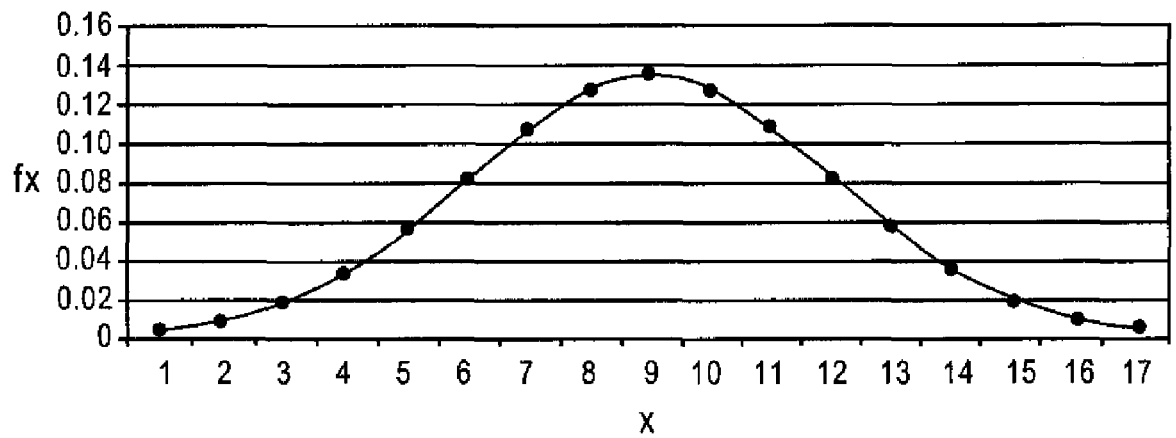
FIG. 5 is a block diagram illustrating an exemplary Gaussian kernel.

FIG. 5 is a block diagram 64 illustrating a Gaussian kernel. In one embodiment of the invention, a Gaussian kernel of sigma three is used as is illustrated in Equation 3. However, the present invention is not limited to this embodiment another other Gaussian kernels can also be used to practice the invention.

$$\text{Gaussian kernel } f(x)=\text{power}(e-\text{constant}G*x*x/(\text{Sigma}*\text{Sigma}))/(\text{Sigma}*\text{sqrt}(2*\text{pi})) \quad (3)$$

Where e="2.71828 . . . " and constantG–0.5. However, the present invention is not limited to a constantG of 0.5 and other values can be used to practice the invention. A Gaussian kernel is used for convolution with a modified image as is illustrated in Equation 4.

$$G=x=(\text{kernelsize}/2) \; x=\text{kernselsize}/2.\text{times}.f.\text{function}.(x)*Ix, \quad (4)$$

where "G" is a Gaussian value at a color position, "kernel size"=1+2*ceiling (2.5*Sigma) and "Ix" is a pixel value at x. Pixels that are on a curve of symmetry of epithelial cell or epithelial area are marked. Typically there will be two curves of symmetry, one parallel to x-axis and the other parallel to y-axis. Pixels belonging to an area of interest are selected based on the intensity. Pixels with intensity value less than (Mean+Standard Deviation) of the image are selected as pixels belonging to an area of interest.

Pixels that are on a curve of symmetry are marked. Typically there will be two curves of symmetry, one parallel to x-axis and the other parallel to y-axis. Pixels belonging to region of interest are selected based on the intensity. Pixels with intensity value less than (Mean+Standard Deviation) of the image are selected as pixels belonging to an area of interest.

A selected pixel is considered to be on the curve of symmetry (i.e., horizontal) only if the pixel's intensity value is less than five neighboring pixels intensity values in a upper direction and five neighboring pixel intensity values in a lower direction. Table 3 illustrates selection of pixel "F".

TABLE 3

A
B
C
D
E
F
G
H
I

TABLE 3-continued

| J |
|---|
| K |

In Table 3, the intensity value of Pixel F, should be less than or equal to the intensity values pixels A, B, C, D, E, G, H, I, J and K.

A selected pixel is considered to be on the curve of symmetry (i.e. vertical) only if a pixel intensity value is less than five neighboring pixels in first (e.g., left of) direction and five neighboring pixels intensity value in a second direction (e.g., right of). That is, in a row of eleven pixels, the intensity value of pixel F should be less than or equal to the intensity values pixels A, B, C, D, E, G, H, I, J and K as is illustrated in Table 4.

TABLE 4

| A | B | C | D | E | F | G | H | I | J | K |
|---|---|---|---|---|---|---|---|---|---|---|

Cell boundaries are identified using a center and two symmetry curves. Curves of symmetry have breaks at the boundary of region of interest. However, if two adjacent cells are touching or overlapping (i.e., which is frequent), there will be no break in the curves of symmetry. In such cases, a mid-point is used on symmetry curve joining two cell centers (i.e., adjacent cells) for identifying cell boundary. An extent of each cell is marked. Marking a cell is done by cropping image starting from a cell center. Cropping is stopped once a pixel intensity is brighter than a limit (i.e., with use mean–standard deviation) or the bounding box of the cell is reached. A bounding box of a cell is determined based on the two symmetry curves. Such Cell boundaries are used to remove stromal cells 36 and lymph cells 38 from further consideration.

Elongation ratios are also used to segment the enhanced digital image 20 to remove unwanted cells from consideration. An elongation ratio is computed for the plural segmented objects. In the case of isolated cells, each object might correspond to a cell. An elongation ratio is the ratio of major axis over minor axis. A major axis is in the direction of the longest line that could be drawn in the object. A minor axis is a line perpendicular to the major axis. Normally a minor axis is drawn through the center of the object. It is observed that shortest line perpendicular to major axis does not pass through the objects representing cells. Lengths of all lines perpendicular to major axis and intersect major axis at any point on the major axis are determined. The least of all of these perpendicular lines as minor axis are considered.

Stromal cells 36 are much longer than they are wide. Thus, an elongation ratio can be used to identify and remove stromal cells 36. Stromal cells 36 are identified that are elongated and are in the range of about 45 pixels and about 500 pixels. These limits are arrived after detailed study of a large number of digital images 20 at standard resolution. However, the present invention is not limited to this range and other ranges can also be used to practice the invention.

A cell is considered as a stromal cell 36 and a pre-determined type of unwanted cells in the enhanced digital image 20 that are removed from consideration if its elongation ratio is more than factor F as illustrated by Equation 5.

$$F = \max((\log (\text{object area}/\text{Con1})), \text{Con2}) \quad (5)$$

where Con1 is 12 and Con2 is 1.5. However, the present invention is not limited to these constant values and other constants can also be used to practice the invention.

All cell pixels overlapping with any one of the detected stromal cells 36 are also removed from consideration.

FIG. 6 is a flow diagram illustrating an exemplary Method 66 for segmentation of digital images to remove unwanted cells from consideration. In one embodiment, Method 66 is used at Step 46 of Method 42. However, the present invention is not limited to such an embodiment and other methods can also be used to practice the invention at Step 44 of FIG. 3.

In FIG. 6 at Step 68, plural unstained non-epithelial cell pixels are identified in the enhanced digital image 20. At Step 70, plural connected non-epithelial unstained cell pixels are identified based on a pre-determined IHC pattern. At Step 72, the plural connected unstained non-epithelial cell pixels are removed from further consideration in the enhanced digital image 20. In one embodiment of the invention, plural unstained epithelial cells 32 are removed from consideration. In another embodiment, Method 66 can be used for any type of unstained cells pixels and is not limited to unstained non-epithelial cell pixels.

Method 66 is illustrated with one exemplary embodiment. However, the present invention is not limited to such an embodiment and other embodiments can also be used to practice the invention.

At Step 68, a stained or non-stained pixel designation is directly determined by a type of IHC compound being used. In one embodiment, H/E staining is used so the red and blue color planes are used to determined stained and non-stained pixels. For example, it is known that segmented objects, such as mitotic cells, nuclei are blue in color when stained with H/E staining and other stains. If a biological tissue sample was treated with an IHC compound other than H/E stain, then nuclei or other cell components would appear as a different colors and thus other color planes would be used to practice the invention and determined stained and unstained cells.

In such an exemplary embodiment at Step 68, a given non-epithelial cell pixel is classified as a "non-stained pixel" if a blue color component of pixel is more than 110% of a red color component of the same pixel. However, the present invention is not limited to such an embodiment and other percentages can also be used to determine a non-stained pixel.

Likewise, a given pixel is classified as a "stained pixel" if a red color component of the pixel is more than 110% of a blue color component of the same pixel. However, the present invention is not limited to such an embodiment and other percentages can also be used to determine a stained pixel.

At Step 70, plural connected unstained non-epithelial cell pixels are identified based on a pre-determined IHC pattern. In one embodiment, the unstained cells are connected at a cell component level, which is one level higher than pixel level. However, the present invention is not limited to such an embodiment and other embodiment can also be used to practice the invention.

In one embodiment, the pre-determined IHC pattern includes an "eight connectivity." However, the present invention is not limited to such an embodiment and pre-determined IHC patterns can also be used to practice the invention. A set of pixels are said to be "eight-connected" if there is an eight connectivity between every pair of pixels in the set.

At Step 72, the identified plural connected unstained non-epithelial cell 32 pixels are removed from further consideration in the enhanced digital image 20.

Returning to FIG. 3 at Step 48, plural cells of interest in the enhanced digital image 20 are identified. In one embodiment of the invention, plural epithelial cells 32 are identified. However, the present invention is not limited to this embodiment and other areas of interest can also be identified.

As was discussed above for stromal cells 38, cell pixels that are on a curve of symmetry of epithelial cells 36 or epithelial cell 36 areas are marked. Typically, there will also be two curves of symmetry for epithelial cells 36, one parallel to x-axis and the other parallel to y-axis. Table 5 illustrates steps that are used to mark epithelial cell 36 pixels on these curves. However, the present invention is not limited to the steps illustrated in Table 5, and more fewer or other steps can also be used to practice the invention.

TABLE 5

Blur cell image using Gaussian kernel (Equation 1) with sigma set to twenty. Area of densely packed cells (epithelial cells 32) becomes darker compared to the stromal cell 36 areas.
Mark the horizontal and vertical axis pixels of the epithelial cell 32 areas.
Get mean & standard deviation of the digital image 20.
Apply following two steps for pixel with intensities less than (Mean + Standard Deviation)
If the pixel intensity is less than five neighboring pixels intensities in top direction and five neighboring pixels in bottom direction then pixel is marked as horizontal axis pixel.
If the pixel intensity is less than five neighboring pixels intensities in left direction and five neighboring pixels in right direction then pixel is marked as vertical axis pixel.
Get the maximum intensity of the (horizontal/vertical) axis pixel.

Epithelial cell 36 areas are identified by thresholding the digital image with maximum intensity values of the pixels on all (horizontal/vertical) edges.

FIG. 7 is a flow diagram illustrating a Method 74 for segmentation of digital images to determine plural cells of interest in the enhanced digital image. In one embodiment, Method 74 is used at Step 48 of Method 42. However, the present invention is not limited to such an embodiment and other methods can also be used to practice the invention at Step 48 of FIG. 3.

In FIG. 7 at Step 76, plural identified stained cells of interest in an enhanced digital image are segmented into plural connected components. At Step 78, a test is conducted to determine if a connected component from the plural components is greater than a pre-determined number of pixels. If the connected component is greater than or equal to a pre-determined number of pixels, at Step 80, the connected component is split into two or more smaller components using image statistics (e.g., mean and standard deviation) calculated for the digital image. If the connected component is not less than a pre-determined number of pixels, at Step 82 a convex hull is determined for the connected component. At Step 84, a test is conducted to determine if the determined convex hull is greater than or equal to pre-determined limit. If the convex hull is greater than a pre-determined limit, Step 80 is executed. If the determined convex hull is not greater than the pre-determined limit, at Step 86 the connected component is added to a list of probable epithelial cell 36 areas.

Method 74 is illustrated with one exemplary embodiment. However, the present invention is not limited to such an embodiment and other embodiments can also be used to practice the invention.

In such an exemplary embodiment at Step 76, identified stained cells of interest in an enhanced digital image are segmented into plural connected components using one or more of the methods described above.

At Step 78, a test is conducted to determine if a connected component from the plural components is greater than a pre-determined number of pixels. A size of each connected component is calculated based on the number of pixels in the connected component. If the size of a connected component is more than a pre-determined pixel limit, then it is possible that the connected component includes more than one epithelial cell 36 area and needs to be re-segmented at Step 80. In one embodiment of the invention, the pre-determined pixel limit is 500-800 pixels. However, the present invention is not limited to such an embodiment and other pre-determined pixel limits can also be used to practice the invention.

At Step 82, a convex hull is determined for the connected component. Convex hulls are features of a mitotic cell. Normal cells are concave in shape. A ratio of convex hull pixels is measured to a size of the connected component in order to distinguishing between mitotic cells and dying cells (e.g., crimped). Dying cells, which are crimped, have convex hulls, but this convex hull ratio will be very large.

Epithelial cell 36 areas vary by huge margins. Two small epithelial cells 36 areas might be just as a large epithelial cell 36 area. In order to determine if the given connected component is made of single epithelial cell 36 area or multiple epithelial cell 36 areas joined, a convex hull on boundary pixels is measured. Convex hulls are important feature of a connected epithelial cell 36 areas. Individual epithelial cell 36 areas are concave in shape. A ratio of convex hull pixels to the size of the connected component is measured to determine if the connected component is made of single epithelial cell 36 area or is a group of connected epithelial cell 36 areas.

It is known in the digital image processing arts, to utilize the concept of a "convex hull" for boundary description in digital pictures. For example, Gonzalez, R. C and Woods R. E, in "Digital Image processing", Pearson education, 2003, pages 653-655 has described a method using the change in slope for detecting convex curve in boundary. However, in the current embodiment, a neighborhood based operator is used instead of a change in slope for a convex hull. Neighbor hood based operations on binary images are faster and more efficient compared to sequential operations like finding slope at a pixel. All identified connected components are considered as two level image objects and analyzed for convex hull. Neighborhood operations are implemented using 3×3 masks. However, the present invention is not limited to this embodiment and other types of neighborhood operations and mask sizes can also be used to practice the invention.

FIG. 8 is a block diagram 88 of exemplary neighborhood masks used with convex hulls. A 3×3 pixel mask centered around every pixel on a boundary of the connected component is considered to determine if the pixel belongs to convex part of the object. A connected component in this context is a two level image, where a value one implies it is a pixel on the mitotic cell and a vale of zero implies it is a pixel not on the mitotic cell. A pixel with a value of zero having three neighbors all with value of one could be identified as a pixel in the convex hull of the connected component. There are four variations in the mask pattern to accommodate the possible permutations 90, 92, 94, 96. However, more, fewer of other variations could also be used to practice the invention.

FIG. 11 is a block diagram 98 illustrating an example of convex hull part 122 in a mitotic cell boundary. The convex hull part 100 is darker in color. A convex hull is typically dark in color in an enhanced digital image 20. A pixel mask (e.g., 3×3 pixels) is applied centered around every pixel on a boundary of a connected component There are four variations in the mask pattern to accommodate the possible permutations. A pixel is identified as pixel on convex hull part of boundary if it satisfies any of the four masks. The ratio of pixels is used satisfying convex hull condition over the connected component size. Let $H_f$ be the convex hull factor defined as is illustrated in Equation (6).

$$H_f = (\text{number of pixels on a convex hull})/(\text{number of pixels in a connected component}) \qquad (6)$$

Returning to FIG. 7, at Step 84, a test is conducted to determine if the determined convex hull is greater than or equal to predetermined limit. In one embodiment, the predetermined limit is 800 pixels. However, the present is not limited to this predetermined limit and other pre-determined limits can also be used to practice the invention.

If the convex hull is greater than a pre-determined limit, Step 80 is executed. If the determined convex hull is not greater than the predetermined limit, at Step 86 the connected component is added to a list of probable epithelial cell 36 areas.

At Step 50, one or more areas of interest in the identified plural epithelial cells 36 in the enhanced digital image 20 are identified. In one embodiment, epithelial cell areas are identified as areas of interest.

Figure 9B:
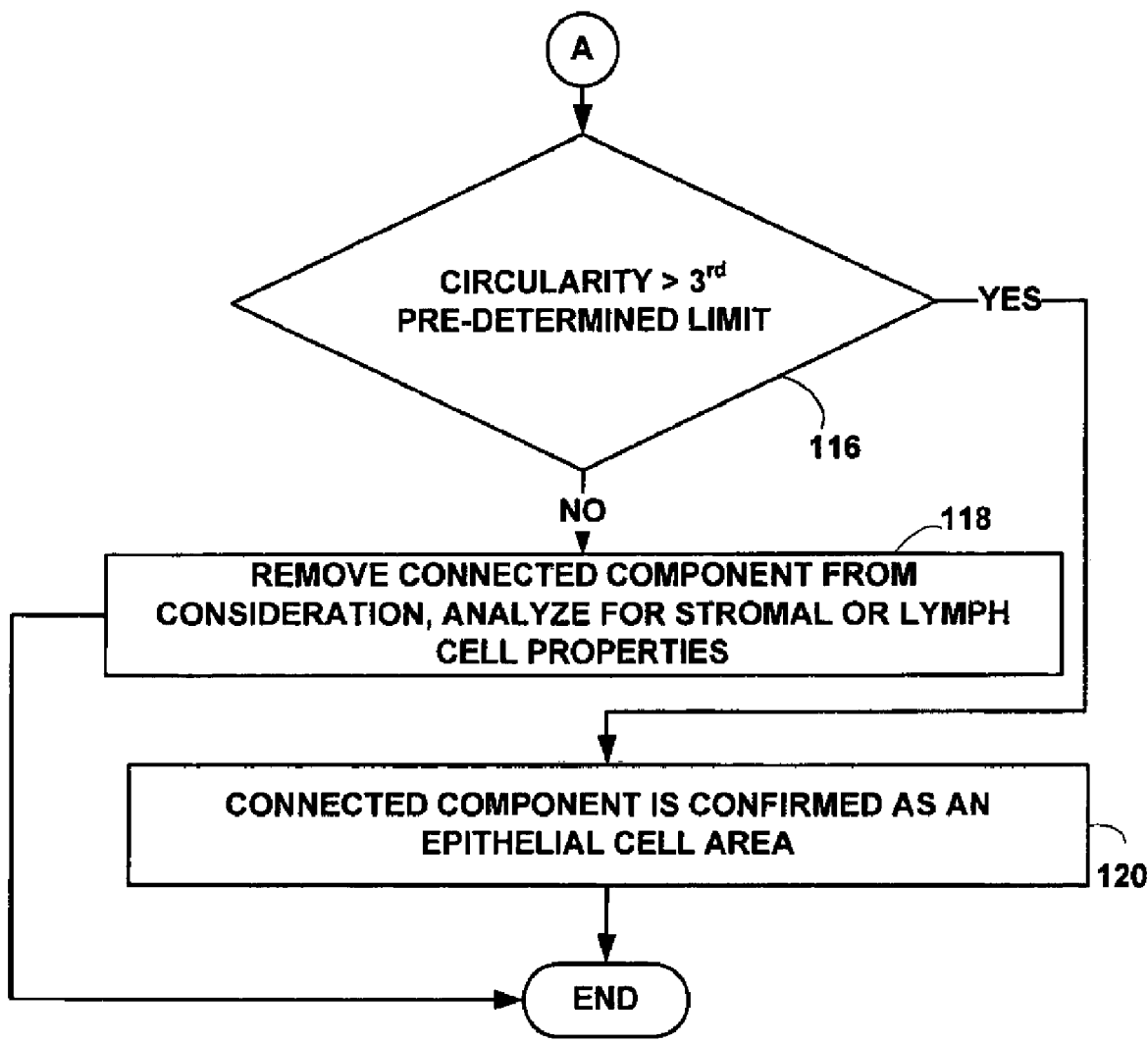

FIGS. 9A and 9B are a flow diagram illustrating a Method 102 for detecting epithelial cell areas from connected components identified with Method 74 of FIG. 7. In one embodiment, Method 102 is used at Step 50 of Method 42. However, the present invention is not limited to such an embodiment and other methods can also be used to practice the invention at Step 50 in FIG. 3.

In FIG. 9A at Step 104, a number of pixels in each of plural connected components is calculated. At Step 106, a test is conducted to determine if the calculated number of pixels in a connected component is greater than or equal to a first pre-determined number of pixels. If the calculated number of pixels is greater than or equal the first pre-determined number of pixels, the connected component is removed from consideration at Step 108. At Step 110, a test is conducted to determine if the calculated number of pixels is less than a second pre-determined limit. If the calculated number of pixels is not less than the second pre-determined limit at Step 112, a lymph cell is detected and the connected component is removed from consideration. If the calculated number of pixels is less than the second pre-determined limit a circularity is calculated for the connected component at Step 114.

In FIG. 9B at Step 116, a test is conducted to determine if the circularity is greater than a third pre-determined limit. If the circularity is not greater than a third pre-determined limit, at Step 118 the connected component is removed from consideration and the connected component is analyzed for stromal cell 36 or lymph cell 38 properties. If the circularity is greater than a third pre-determined limit, at Step 120, the connected component is confirmed as an epithelial cell 32 area.

Method 102 is illustrated with one exemplary embodiment. However, the present invention is not limited to such an embodiment and other embodiments can also be used to practice the invention.

In such an exemplary embodiment at FIG. 9A at Step 104, a number of pixels a connected components is calculated. At Step 106, a test is conducted to determine if the calculated number of pixels in a connected component is greater than or equal to a first pre-determined number of pixels. In one embodiment, the first pre-determined number of pixels is 800. However, the present invention is not limited to such an embodiment and other values for the first pre-determined number of pixels can also be used to practice the invention.

If the calculated number of pixels is greater than or equal the first pre-determined number of pixels, the connected component is removed from consideration at Step 108. The connected component has large sized features and is thus analyzed for artifact 40 features.

At Step 110 a test is conducted to determine if the calculated number of pixels is less than a second pre-determined number of pixels. In one embodiment, the second pre-determined limit is 100 pixels. However, the present invention is not limited to such an embodiment and other values for the second pre-determined number of pixels can also be used to practice the invention If the calculated number of pixels is not less than the second pre-determined limit at Step 112, a lymph cell 38 is detected and the connected component is removed from consideration.

If the calculated number of pixels is less than the second pre-determined limit a circularity is calculated for the connected component at Step 114. Circularity is used to identify connected components like artifacts 40, which do not necessarily exhibit circular patterns. A bounding box is drawn around each connected component. Using a bounding box around each connected component, a first pixel on the boundary of connected component is located, then other pixels are traced on the boundary satisfying eight connectivity. The number of connected pixels on a boundary of a connected component gives an accurate estimation of a perimeter of connected component. A number of pixels in a connected component indicates a connected component area.

In one embodiment, circularity is calculated with Equation (7). However, the present invention is not limited to this embodiment and other circularity equations can be used to practice the invention.

$$\text{Circularity} = \text{Con}C \times \text{Pi} \times (\text{connected component pixel size})/(\text{perimeter} \times \text{perimeter}), \qquad (7)$$

where ConC is a constant with value of 4 and Pi has a value of 3.1415927 .... However, the present invention is not limited this constant value and other constant values can be used to practice the invention.

In one embodiment, the third pre-determined limit is 0.9. However, the present invention is not limited to this value and other values can be used for the third pre-determined limit to practice the invention. If the circularity of connected component is greater than 0.9, then it is confirmed as epithelial cell 32 area at Step 120. If the circularity is less than 0.9, then the connected component is removed from consideration and is analyzed for stromal cells 36 and lymph cells 38 at Step 118.

In one embodiment, probable epithelial cell areas of size more than 100 pixels but less than 800 pixels are further analyzed for lymph cell 38 area and stromal cell 36 area properties. Stromal cell 36 areas are thin and elongated, compared to epithelial cell 32 areas which tend to be circular or elliptical in shape.

Figure 10A:
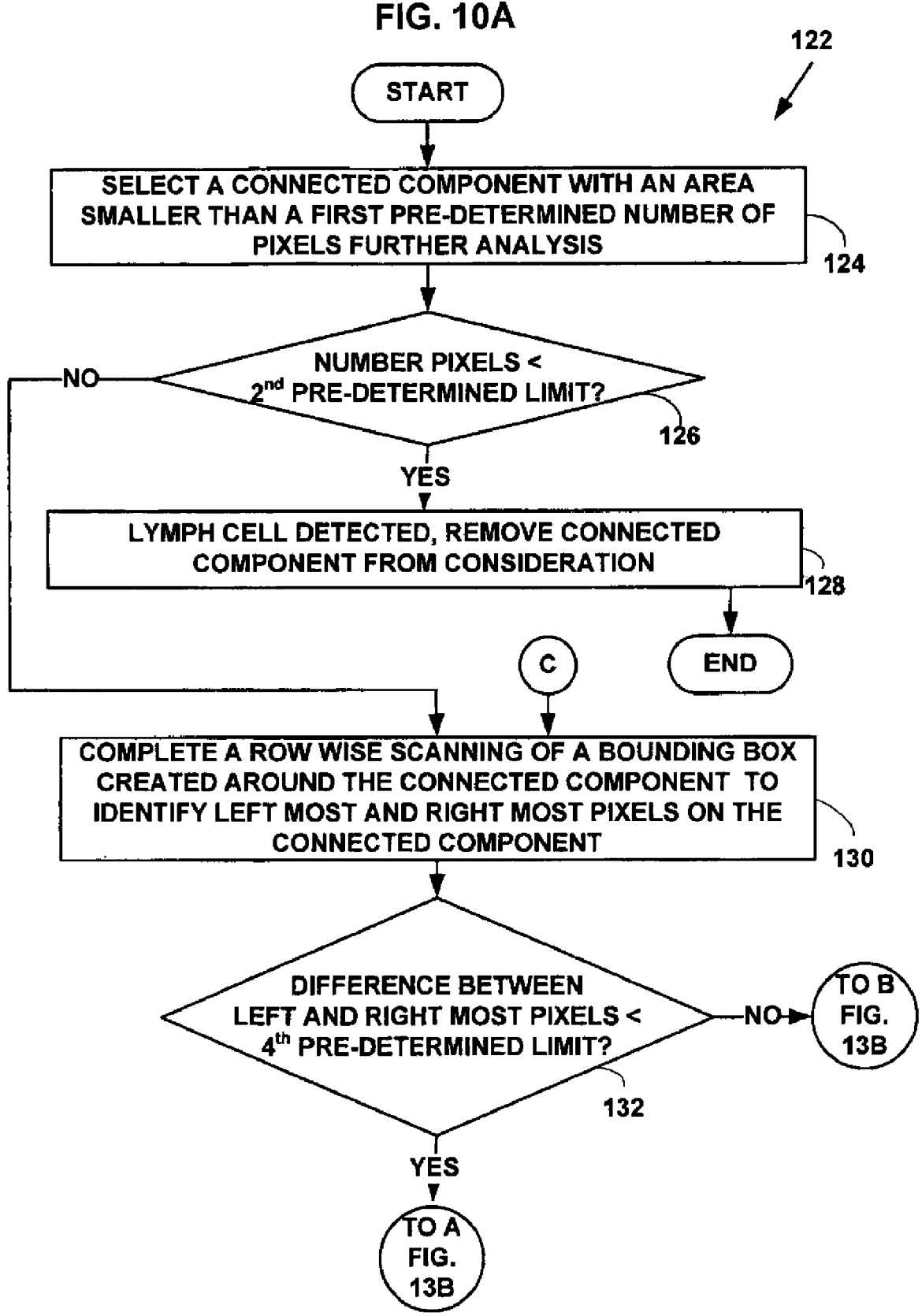
FIGS. 10A and 10B and 10C are a flow diagram illustrating a method for detecting stromal cell areas and lymph cell areas from connected components identified with the method of FIG. 7.
Figure 10B:
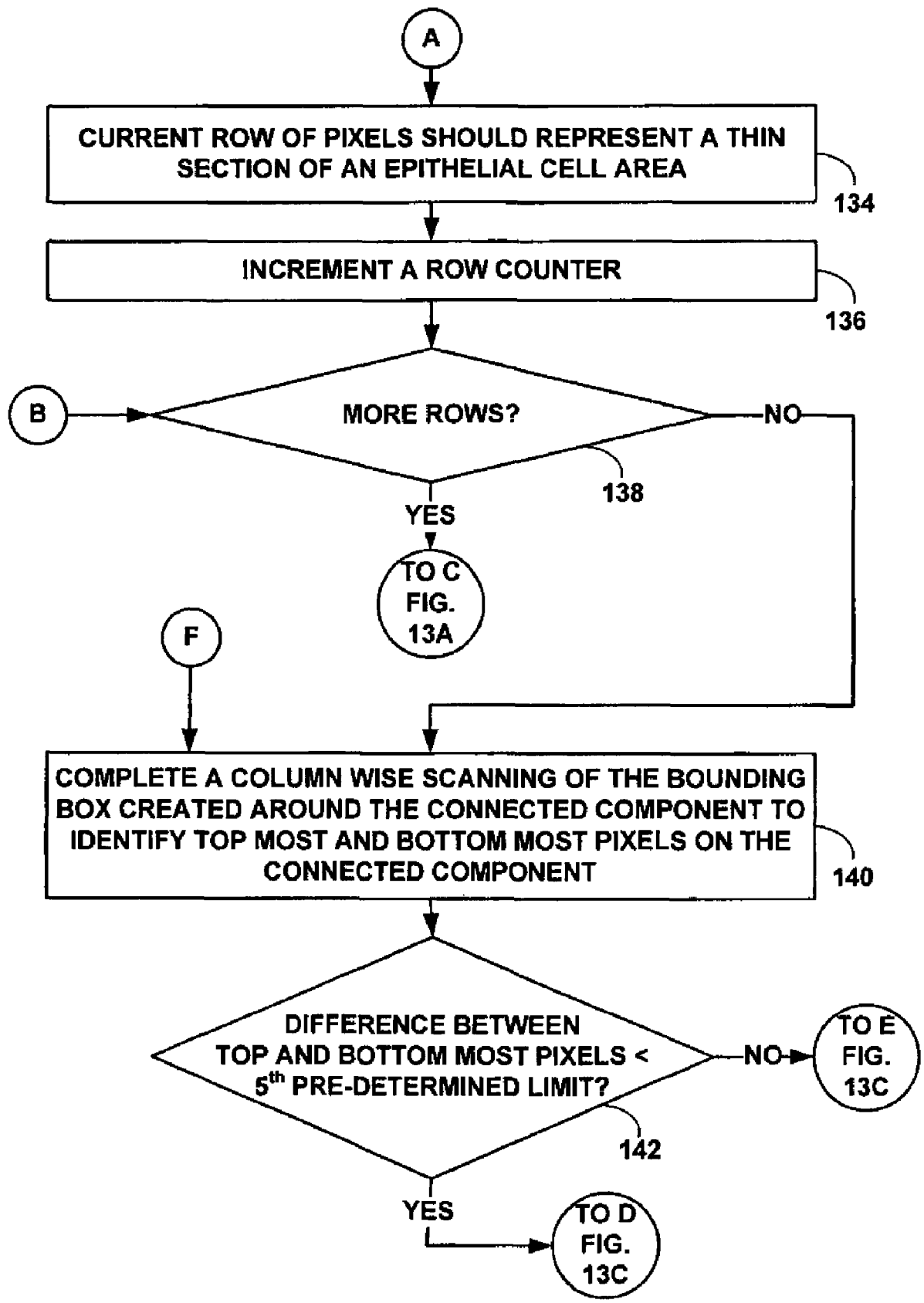
Figure 10C:
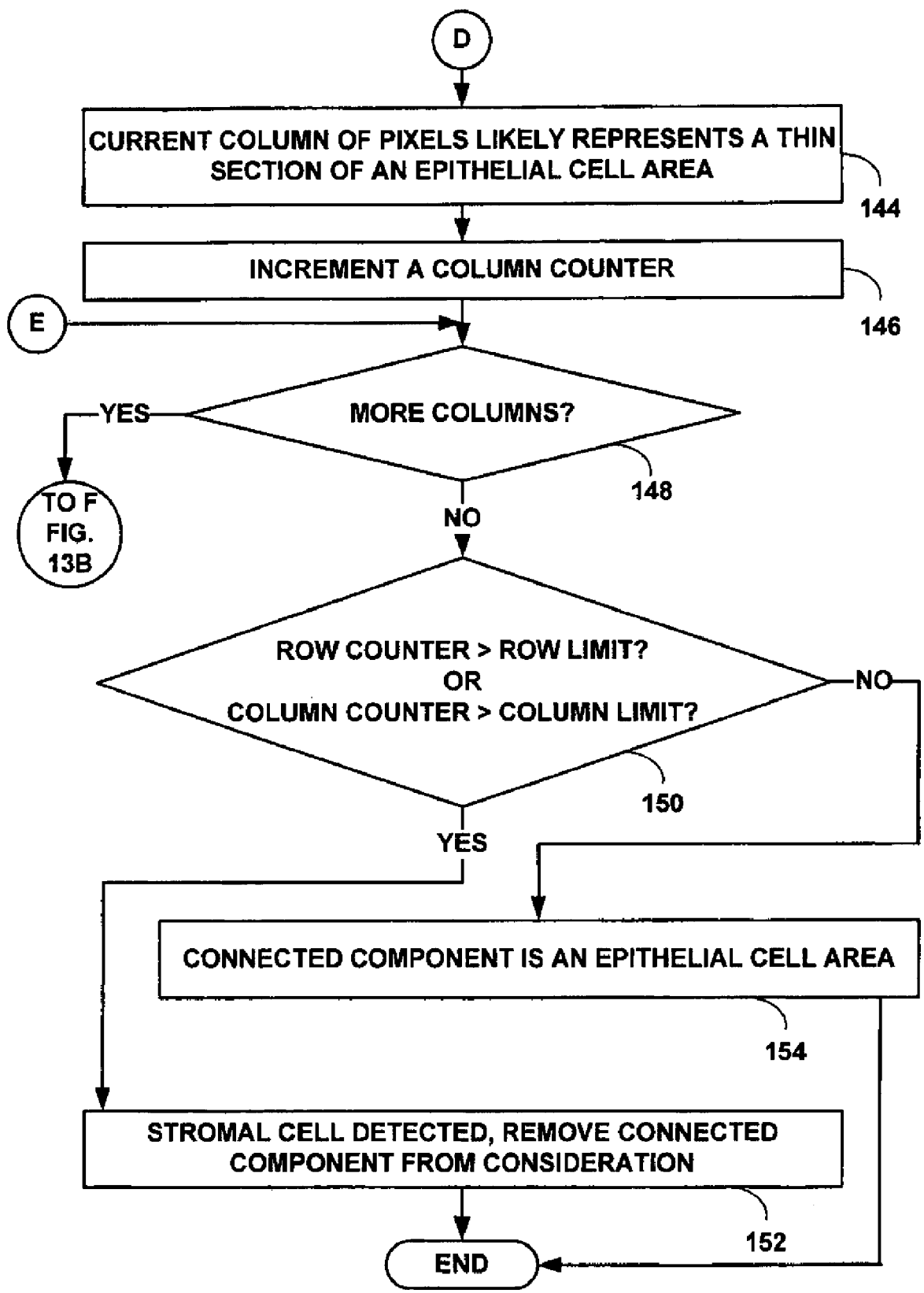

FIGS. 10A, 1013 and 10C are a flow diagram illustrating a Method 122 for detecting stromal cell areas and lymph cell areas within a list of connected components identified as probable epithelial cell areas based on size and shape. In one embodiment, Method 122 is used at Step 50 of Method 42. However, the present invention is not limited to such an embodiment and other methods can also be used to practice the invention at Step 50 in FIG. 3.

In FIG. 10A at Step 124, connected components with an area smaller than the first predetermined number of pixels are selected for further analysis. At Step 126, a test is conducted to determine if a connected component area size is less than the second pre-determined limit. If the connected component area size is less than the second pre-determined limit, at Step 128, the connected component is identified as a lymph cell 38 and removed from consideration.

If the connected component area size is not less than the second pre-determined limit, at Step 130 a row wise scanning of a bounding box created around the connected component is completed to identify left most and right most pixels on the connected component. At Step 132, a test is conducted to determine if a difference between the left most and right most pixels is less than a fourth pre-determined value. If the difference between the left and right pixels is less than a fourth pre-determined limit, the current row of pixels could represent a thin section of an epithelial cell area at Step 134 in FIG. 13B. At Step 136, a row counter is incremented. At Step 138, a test is conducted to determine if there are more rows in the connected component, and if so, Steps 130, 132, 134, 136 and 138 are repeated for all pixels rows of the connected component.

When there are no more rows to be scanned, at Step 140, a column wise scanning of the bounding box created around the connected component is completed to identify top most and bottom most pixels on the connected component. At Step 142, a test is conducted to determine if a difference between the top most and bottom most pixels is less than a fifth pre-determined value.

If the difference between the left and right pixels is less than a fifth pre-determined limit, the current column of pixels could represent a thin section of an epithelial cell 32 area at Step 144 in FIG. 10C. At Step 146 a column counter is incremented. At Step 148, a test is conducted to determine if there are more columns in the connected component, and if so, Steps 140, 142 144, 146 and 148 are repeated for all columns of pixels of the connected component.

When there are no more columns, at Step 150, a test is conducted to determine whether the row counter or the column counter is greater than a row or column pre-determined limit. If the row counter or column counter is greater than a pre-determined limit, a stromal cell 36 has been detected and the connected component is removed from consideration at Step 150. If the row counter or column counter is not greater than a predetermined limit, than the connected component is identified as an epithelial cell area 32 at Step 152.

Method 122 is illustrated with one exemplary embodiment. However, the present invention is not limited to such an embodiment and other embodiments can also be used to practice the invention.

In such an exemplary embodiment in FIG. 10A at Step 124, connected components with an area smaller than the 800 pixels are selected for further analysis. At Step 126, a test is conducted to determine if a connected component area size is less than 100 pixels. If the connected component area size is less than 100 pixels, at Step 128, the connected component is identified as a lymph cell 38 and removed from consideration.

If the connected component area size is not less than 100 pixels, at Step 130 a row wise scanning of a bounding box created around the connected component is completed to identify left most and right most pixels on the connected component. A thickness of a connected component in each row and column of identified probable epithelial cell area is measured to differentiate between stromal cell 36 area and epithelial cell 32 area. At Step 132, a test is conducted to determine if a difference between the left most and right most pixels is less than six pixels. If the difference between the left and right pixels is less than 6 pixels, the current row of pixels could represent a thin section of an epithelial cell area at Step 134 in FIG. 13B. At Step 136, a row counter is incremented. At Step 138, a test is conducted to determine if there are more rows in the connected component, and if so, Steps 130, 132, 134, 136 and 138 are repeated for all pixels rows of the connected component.

When there are no more rows to be scanned, at Step 140, a column wise scanning of the bounding box created around the connected component is completed to identify top most and bottom most pixels on the connected component. At Step 142, a test is conducted to determine if a difference between the top most and bottom most pixels is less than six pixels.

If the difference between the left and right pixels is less than six pixels the current column of pixels could represent a thin section of an epithelial cell 32 area at Step 144 in FIG. 10C. At Step 146 a column counter is incremented. At Step 148, a test is conducted to determine if there are more columns in the connected component, and if so, Steps 140, 142 144, 146 and 148 are repeated for all columns of pixels of the connected component.

When there are no more columns, at Step 150, a test is conducted to determine whether the row counter or the column counter is greater than a row or column pre-determined limit. If the row counter or column counter is greater than 100, a stromal cell 36 has been detected and the connected component is removed from consideration at Step 150. If the row counter or column counter is not greater than 100 pixels, than the connected component is identified as an epithelial cell area 32 at Step 152.

Returning to FIG. 3 at step 52, cell artifacts 40 from the one or more identified areas of interest are removed from consideration, thereby creating one or more enhanced areas of interests used for creating a medical diagnosis or prognosis. Artifacts 40 are usually very large and have a different type of texture compared to epithelial cells 32.

A red color plane of a typical digital image 20 carries necessary variation between artifacts 40 and epithelial cells 32. Detecting artifacts 40 within the areas of interest is based in part on gradient, and run lengths of connected pixels in a row and roughness of a boundary of an area of interest. Epithelial cells 32 have variations in intensity across the cell area. This is because of variation in opacity of nucleus, cytoplasm and membrane, three basic compartments of an epithelial cell 32. Artifacts 40, which are essentially dead cells, folded tissues or some other fluid drops, do not have the kind of variations observed in epithelial cell 32 areas.

FIGS. 11A and 11B are a flow diagram illustrating an exemplary Method 156 for removing artifacts 40. In one embodiment, Method 156 is used at Step 52 of Method 42. However, the present invention is not limited to such an embodiment and other methods can also be used to practice the invention at Step 52 in FIG. 3.

In FIG. 11A at Step 158, a gradient is calculated within an area of interest. At Step 160, a run length ratio is calculated within the area of interest. At Step 162, a test is conducted to determine if the gradient is less than a first limit and the run length ratio is greater than a second limit. If the gradient is less than a gradient limit and the run length ratio is greater than a ratio limit, at Step 164 the area of interest is confirmed to be an epithelial cell 32 area of interest without artifacts 40. If the gradient is not less than the gradient limit or the run length ratio is not greater than the ratio limit at Step 166 a test is conducted to determine if the area of interest is adjacent to a non-area of interest. If the area of interest is adjacent to a non-area of interest, at Step 168, the area of interest is determined to be folded tissue and is removed from consideration.

In FIG. 11B, if the area of interest is not adjacent to a non-area of interest, at Step 170, a spike count is computed for the area of interest. At Step 172, a test is conducted to determine if a spike count is greater than a spike limit. If the spike count is greater than the spike limit, at Step 174, the area of interest is identified as an artifact 40 and removed from consideration. lithe spike count is not greater than the spike limit, at Step 176, the area of interest is identified as an epithelial cell 32 area without artifacts 40.

Method 156 is illustrated with one exemplary embodiment. However, the present invention is not limited to such an embodiment and other embodiments can also be used to practice the invention.

In such an exemplary embodiment in FIG. 11A at Step 158, a gradient is calculated within an area of interest. In one embodiment, a minimum and maximum gradient in an area of interest of a cell nucleus in a digital image and a histogram of the gradient of corresponding pixels used are calculated. A first average gradient across the area of interest is calculated. A test is conducted to determine if the calculated maximum gradient is less than a pre-determined gradient or a pre-determined number of pixels with a gradient greater then the pre-determined gradient is less than a pre-determined number, then a calculated gradient variation is set to zero. Otherwise a pre-determined number of pixels having a largest gradient are selected. A second average gradient variation is determined. A calculated gradient is set to (second average gradient—first average gradient). However, other method can be used to calculate the gradient and the present invention is not limited to this embodiment.

At Step 160, a run length ratio is calculated within the area of interest. The run length ratio includes a cumulative frequency of run lengths compared to a run length parameter as a number of pixels. However, the present invention is not limited to this embodiment and other types of run length ratios can also be used to practice the invention. Another property observed in artifacts 40 is continuous run of connected pixels in a probable epithelial cell 32 area while scanning from left to right. In the case of epithelial cell 32 areas, each scan line of a connected component will be fragmented into several run lengths. These fragments are created due to variation in level of expression by various compartments of a cell, or due to vesicular nature of some of the epithelial cells 32. Statistics including ratios of run lengths are computed for row wise in an identified probable epithelial cell 32 area of interest.

At Step 162, a test is conducted to determine if the gradient is less than a 130 and a cumulative frequency of run lengths reaches 100% before a run length parameter reaches 100 pixels. In the case of epithelial cells 32, this cumulative frequency reaches 100%.

If the gradient is less than the gradient limit and the run length ratio is greater than the ratio limit, at Step 164 the area of interest is confirmed to be an epithelial cell 32 area of interest without artifacts 40. If the gradient is not less than the gradient limit or the run length ratio is not greater than the ratio limit at Step 166 a test is conducted to determine if the area of interest is adjacent to a non-area of interest. If the area of interest is adjacent to a non-area of interest, at Step 168, the area of interest is determined to be folded tissue and is removed from consideration.

In FIG. 11B, if the area of interest is not adjacent to a non-area of interest, at Step 170, a spike count is computed for the area of interest. Probable epithelial cell 32 areas not adjacent to a non-tissue area, but have low gradient are analyzed for another feature of artifacts 40. Epithelial cell 32 areas are smooth and concave, where as most of the artifacts 40 have convex parts in their boundary. Artifacts 40 have rough boundary compared to epithelial cell 32 areas. There can be several "spike" like extrusions of tissue with no epithelial cells 32 in these extrusions. A spike in boundary is detected based on boundary pixel and its immediate neighboring pixels in a 3×3 pixel window. Boundary pixels having only one neighboring boundary pixel in 3×3 window are considered as "spike."

At Step 172, a test is conducted to determine if a spike count is greater than a spike limit of 30. If the spike count is greater than the spike limit, at Step 174, the area of interest is identified as an artifact 40 and removed from consideration. If the spike count is not greater than the spike limit, at Step 176, the area of interest is identified as an epithelial cell 32 area without artifacts 40.

FIG. 12 is a flow diagram illustrating a Method 178 for automated digital image analysis for identifying epithelial cell areas in immunohistochemical patterns. At Step 180, luminance values of plural pixels from a digital image of a human tissue sample to which an IHC compound has been applied are analyzed to segment the digital image into an IHC pattern area and background area. At Step 182, one or more probable epithelial cell areas are identified in the segmented IHC pattern area. At step 184, stromal cell 36 areas and lymph cell 38 areas within the one or more identified probable epithelial cell areas are detected and filtered out to create one or more filtered probable epithelial cell areas. At step 186, artifact 40 areas from the one or more filtered probable epithelial cell areas are detected and filtered out. At Step 188, a medical conclusion is created from the one or more filtered probable epithelial cell areas.

Method 178 is illustrated with one exemplary embodiment. However, the present invention is not limited to such an embodiment and other embodiments can also be used to practice the invention.

In such an exemplary embodiment at Step 180, luminance values of plural pixels from a digital image of a human tissue sample to which an IHC compound has been applied are analyzed to segment the digital image into an IHC pattern area and background area with Methods 54, and 66. At Step 182, probable epithelial cell areas are identified in the segmented IHC pattern area with Method 74. At step 184, stromal cell 36 areas and lymph cell 38 areas within the identified probable epithelial cell areas are detected and filtered out with Methods 102 and 122 to create one or more filtered probable epithelial cell 32 areas. At step 186, artifact 40 areas from the one or more filtered probable epithelial cell areas are detected and filtered out with Method 156. At Step 188, a medical conclusion is created using the one or more filtered probable epithelial cell areas. The medical conclusion includes a medical diagnosis or prognosis, such as for a human cancer, and/or a life science conclusion and biotechnology experiment conclusion.

In one embodiment of the invention, step 180 is completed with a first software module as a pre-processing module. The remaining steps 182-188 are completed with a second software module. However, the present invention is not limited to this embodiment and more, fewer or other combinations of software modules can be used to practice the invention.

Figure 13A:
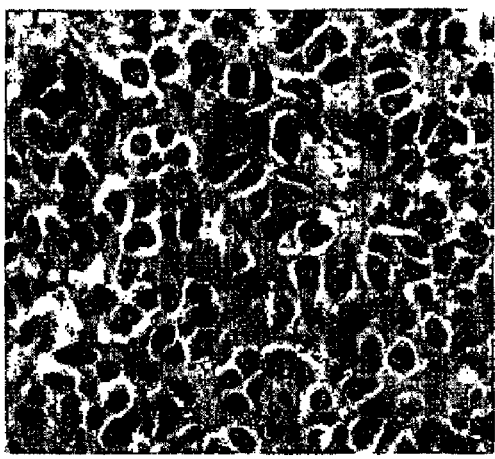
FIGS. 13A-13D are a block diagram illustrating epithelial cell areas identified within areas of interest.
Figure 13B:
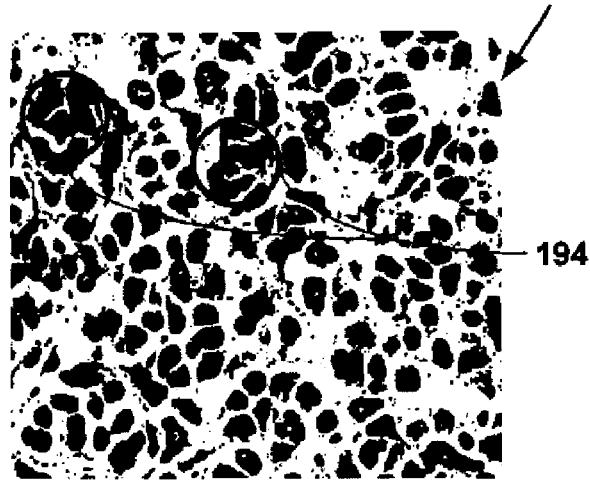
Figure 13C:
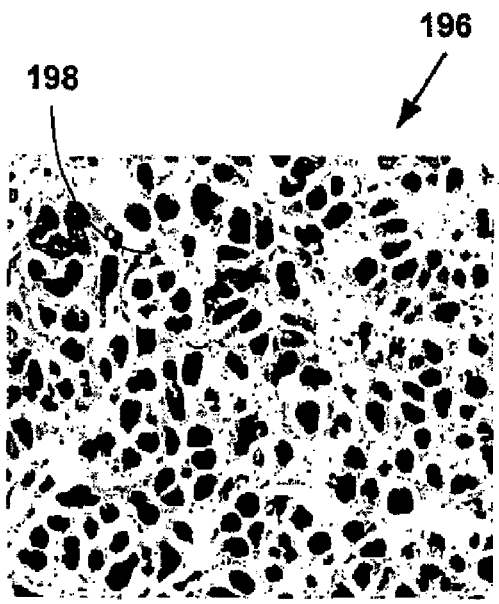
Figure 13D:
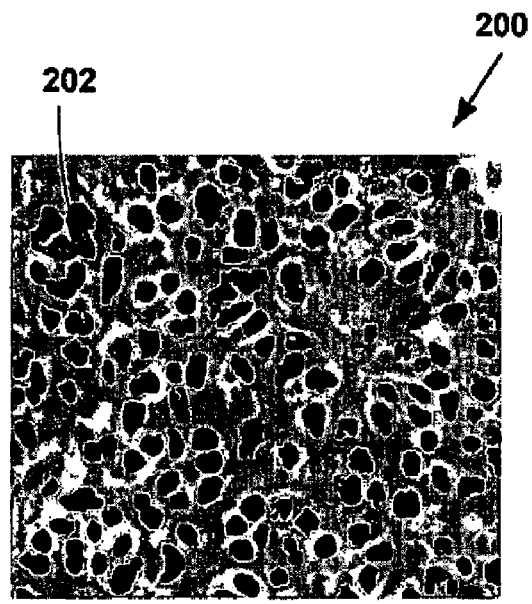

FIGS. 13A-13D are a block diagrams illustrating epithelial cell 32 areas identified within areas of interest. FIG. 13A illustrates an original digital image 190. FIG. 13B 192 illustrates plural segmented connected components 194. FIG. 13C 196 illustrate examples of stromal cell 36 areas deleted from the list of probable epithelial cell 32 areas. The stromal cell 36 areas are lighter in color as is illustrated once by 198. FIG. 13D 200 illustrates the automated result where all epithelial cell 32 areas in a digital image 20 are identified. The identified epithelial cell areas 32 are darker in color as is illustrated once by 202.

Figure 14:
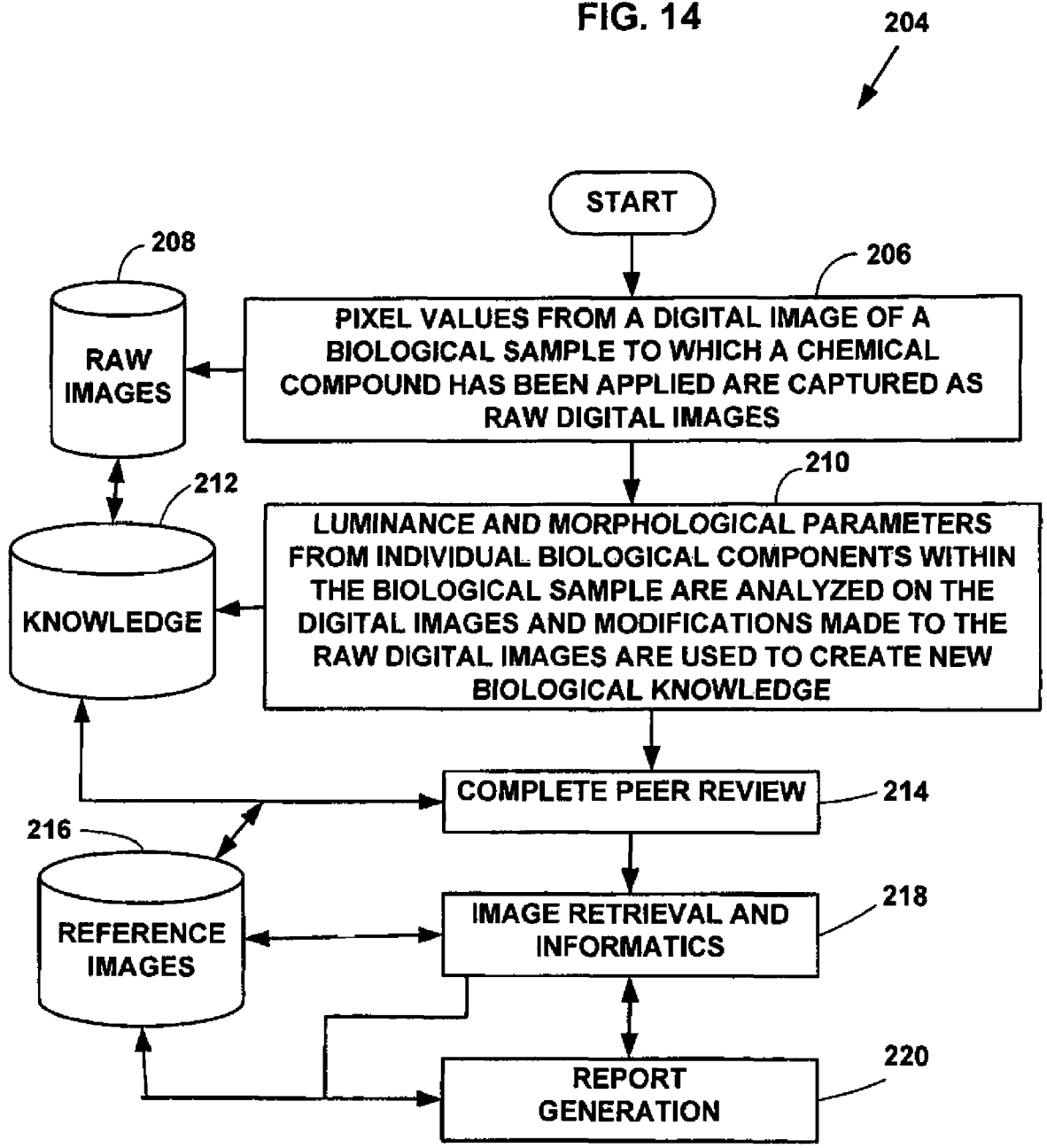
FIG. 14 is a block diagram illustrating an exemplary flow of data in the automated IHC analysis system.

FIG. 14 is a block diagram illustrating an exemplary flow of data 204 in the exemplary automated digital image based epithelial detection and classification system 10. Pixel values from a digital image of a biological sample to which a IHC compound has been applied are captured 206 as raw digital images 208. The raw digital images are stored in raw image format in one or more image databases 18. Luminance and morphological parameters from individual biological components within the biological sample are analyzed on the digital image and modifications made to the raw digital images are used to create new biological knowledge 210 using the methods described herein. The new biological knowledge is stored in a knowledge database 212. Peer review of the digital image analysis and life science and biotechnology experiment results is completed 214. A reference digital image database 216 facilitates access of reference images from previous records of life science and biotechnology experiments at the time of peer review. Contents of the reference digital image database 216, information on the biological sample and analysis of current biological sample are available at an image retrieval and informatics module 218 that displays information on GUI 14. Conclusions of a medical diagnosis or prognosis or life science and biotechnology experiment are documented as one or more reports. Report generation 220 allows configurable fields and layout of the report. New medical knowledge is automatically created.

The present invention is implemented in software. The invention may be also be implemented in firmware, hardware, or a combination thereof, including software. However, there is no special hardware or software required to use the proposed invention.

The automated methods and system described herein may detects epithelial cells 32 including even small epithelial areas that human pathologists might skip or overlook. It filters stromal cells 36, lymph cells 48 and artifacts 40 from an enhanced digital image 20 of a tissue sample to which an IHC compound has been applied and includes an image enhancer that accommodates for low contrast images. It may also be used to detect isolated epithelial cells 32.

The method and system described herein helps differentiate an epithelial cell 32 part from a non-epithelial cell part 36, 38, 40 of a digital image 20 of a tissue sample to which an IHC compound has been applied. The method and system help correct errors in the interpretation of the analysis of tissue samples for diseases such as human cancers.

It should be understood that the architecture, programs, processes, methods and systems described herein are not related or limited to any particular type of computer or network system (hardware or software), unless indicated otherwise. Various types of general purpose or specialized computer systems may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams.

While various elements of the preferred embodiments have been described as being implemented in software, in other embodiments hardware or firmware implementations may alternatively be used, and vice-versa.

The claims should not be read as limited to the described order or elements unless stated to that effect. In addition, use of the term "means" in any claim is intended to invoke 35 U.S.C. §112, paragraph 6, and any claim without the word "means" is not so intended.

Therefore, all embodiments that come within the scope and spirit of the following claims and equivalents thereto are claimed as the invention.

We claim:

1. An automated method for automated detection of immunohistochemical patterns, comprising: enhancing a digital image of a biological sample to which an immunohistochemical (IHC) compound has been applied; wherein the enhancing step includes: computing digital image statistics of pixel values for each of red, green and blue color planes independently in the digital image; determining whether a standard deviation from the computed digital image statistics in each of the red, green and blue color planes is less than a predetermined value, and if so, determining a maximum intensity value of an original range of intensity values using a distribution of pixel values in the red, green and blue color planes independently; and mapping pixel values in each color plane such that pixel values in an original range of intensity values are mapped to an enhanced range of intensity values to contrast enhance the digital image, removing pre-determined types of unwanted cells in the enhanced digital image from consideration; wherein the step of removing pre-determined types of unwanted cells in the enhanced digital image from consideration includes: segmenting the enhanced digital image into a plurality of objects using a pre-determined Gaussian kernel; calculating a plurality of elongation ratios for the plurality of objects; and removing the pre-determined types of unwanted cells using the calculated plurality of elongation ratios, identifying a plurality of cells of interest in the enhanced digital image; wherein the step of identifying a plurality of cells of interest in the enhanced digital image includes: segmenting the enhanced digital image into a plurality of objects using a pre-determined Gaussian kernel; calculating a plurality of curves of symmetry for the plurality of objects; and identifying the plurality of cells of interest using the calculated plurality of curves of symmetry, identifying one or more areas of interest in the identified plurality of cells of interest in the enhanced digital image; and removing cell artifacts from consideration in the one or more identified areas of interest, thereby creating and displaying one or more enhanced areas of interests used for creating a medical diagnosis or prognosis.

2. The method of claim 1 further comprising providing a computer readable medium having stored therein instructions for causing one or more processors to execute the steps of the method.

3. The method of claim 1 wherein the IHC compound includes a Haematoxylin and Eosin (WE) stain.

4. The method of claim 1 wherein the predetermined types of unwanted cells include stromal cells or lymph cells.

5. The method of claim 1 wherein the cells of interest include epithelial cells.

6. The method of claim 1 wherein the step of identifying a plurality of cells of interest includes identifying a plurality of cells of interest including estrogen receptors (ER) or progesterone receptors (PR) reacting to the IHC compound.

7. The method of claim 1 wherein the step of identifying a plurality of cells of interest includes identifying a plurality of cells of interest including Her2/neu receptors reacting to the IHC compound.

8. The method of claim 1 wherein the biological sample includes a plurality of human cells.

9. The method of claim 8 wherein the plurality of human cells potentially includes one or more human cancer cells.

10. The method of claim 9 wherein the one or more human cancer cells are breast cancer cells.

11. The method of claim 1 wherein the medical diagnosis or prognosis includes a diagnosis or prognosis for a human cancer.

12. The method of claim 1 wherein the step of removing pre-determined types of unwanted cells in the enhanced digital image from consideration includes: segmenting the enhanced digital image into a plurality of objects using a pre-determined Gaussian kernel; calculating a plurality of curves of symmetry for the plurality of objects; and removing the pre-determined types of unwanted cells using the calculated plurality of curves of symmetry.

13. The method of claim 1 wherein the unwanted cells include stromal cells.

14. The method of claim 1 wherein the step of removing pre-determined types of unwanted cells in the enhanced digital image from consideration includes: identifying a plurality of unstained cell pixels in the enhanced digital image; identifying a plurality of connected unstained cell pixels based on a pre-determined IHC pattern; and removing the identified plurality of connected unstained cell pixels from further consideration in the enhanced digital image.

15. The method of claim 14 wherein the unstained cell pixels include unstained non-epithelial cell pixels.

16. The method of claim 15 wherein the pre-determined IHC pattern includes an eight connectivity between unstained non-epithelial cell pixels.

17. The method of claim 1 wherein the step of identifying a plurality of cells of interest in the enhanced digital image includes: segmenting the enhanced digital image into a plurality of connected components of cells of interest; determining a plurality of convex hulls for the plurality of connected components; identifying the plurality of cells of interest using the determined plurality of convex hulls.

18. The method of claim 17 where the plurality of cells of interest include stained epithelial cells.

19. The method of claim 17 wherein the step of determining a plurality of convex hulls for the plurality of connected components includes: centering a plurality of neighborhood masks around a plurality of pixels on a boundary of a cell from a connected component; and determining whether the plurality of pixels on the boundary of the cell belong to a convex hull of the cell, and if so, calculating a convex hull factor.

20. The method of claim 17 wherein the neighborhood masks include three-by-three neighborhood masks.

21. The method of claim 1 wherein the step of identifying one or more areas of interest in the identified plurality of cells of interest in the enhanced digital image includes: segmenting the enhanced digital image into a plurality of connected components of cells of interest; calculating a number of pixels in a connected component; calculating a circularity of the connected component; and determining with the calculated number of pixels and calculated circularity whether the connected component includes an epithelial cell area.

22. The method of claim 1 wherein the step of identifying one or more areas of interest in the identified plurality of cells of interest in the enhanced digital image includes: segmenting the enhanced digital image into a plurality of connected components of cells of interest; scanning a plurality of rows in a connected component; scanning a plurality of columns of the connected component; and determining with a number of scanned rows or a number of scanned columns whether the connected component includes an epithelial cell area.

23. The method of claim 1, wherein the step of removing cell artifacts from consideration in the one or more identified areas of interest includes: calculating a gradient within an identified area of interest; calculating a run length ratio within the identified area of interest; calculating a spike count within the identified area of interest; and removing artifacts from the identified area of interest using the calculated gradient, run length ratio and spike counts, thereby leaving an identified area of interest identified as an epithelial cell area without artifacts.

* * * * *